(12) United States Patent
Nichols et al.

(10) Patent No.: US 9,572,678 B2
(45) Date of Patent: Feb. 21, 2017

(54) TISSUE SPACER IMPLANTS, INSERTION AND ADJUSTMENT TOOLS, AND METHOD OF USE

(71) Applicant: MEDIVEST, LLC, Columbia City, IN (US)

(72) Inventors: Ross Nichols, North Webster, IN (US); Brian G. Emerick, Columbia City, IN (US); Brent Walter, Huntington, IN (US); Larry Sutton, Columbia City, IN (US); Heidi Stamets, Monroeville, IN (US)

(73) Assignee: MEDIVEST, LLC, Columbia City, IN (US)

( * ) Notice: Subject to any disclaimer, the term of this patent is extended or adjusted under 35 U.S.C. 154(b) by 370 days.

(21) Appl. No.: 14/377,212

(22) PCT Filed: Feb. 7, 2013

(86) PCT No.: PCT/US2013/025134
§ 371 (c)(1),
(2) Date: Aug. 7, 2014

(87) PCT Pub. No.: WO2013/119803
PCT Pub. Date: Aug. 15, 2013

(65) Prior Publication Data
US 2015/0018957 A1    Jan. 15, 2015

Related U.S. Application Data

(60) Provisional application No. 61/595,755, filed on Feb. 7, 2012.

(51) Int. Cl.
| | | |
|---|---|---|
| *A61F 2/44* | (2006.01) | |
| *A61F 2/46* | (2006.01) | |
| *A61F 2/28* | (2006.01) | |
| *A61F 2/30* | (2006.01) | |

(52) U.S. Cl.
CPC ............. *A61F 2/4425* (2013.01); *A61F 2/44* (2013.01); *A61F 2/4455* (2013.01);
(Continued)

(58) Field of Classification Search
CPC ....................................................... A61F 2/44
(Continued)

(56) References Cited

U.S. PATENT DOCUMENTS

| | | | | |
|---|---|---|---|---|
| 6,193,755 B1 * | 2/2001 | Metz-Stavenhagen | ... | A61F 2/44 623/17.11 |
| 6,193,756 B1 * | 2/2001 | Studer | ....................... | A61F 2/44 623/17.15 |

(Continued)

OTHER PUBLICATIONS

International Search Report for PCT/US2013/025134 dated May 29, 2013.

*Primary Examiner* — David Bates
(74) *Attorney, Agent, or Firm* — Heslin Rothenberg Farley & Mesiti P.C.; John W. Boger

(57) ABSTRACT

Tissue spacer implants and surgical methods for inserting the implants are disclosed. The implants may include a first cylindrical body with an outer surface, an axially extending hole, and a first end, a second cylindrical body with an outer surface and an axially extending hole, and an adjustment member with an outer surface, an axial hole, and at least one helical slot. The adjustment member axial hole may be adapted to receive the first cylindrical body and the adjustment member may be configured to be inserted into the axially extending hole of second cylindrical body. The implants may also include a travel mechanism for engaging the first cylindrical body, adjustment member, and second cylindrical body along the at least one helical slot to maintain a space between two bodies of tissue.

19 Claims, 27 Drawing Sheets

(52) U.S. Cl.
CPC .......... *A61F 2/4465* (2013.01); *A61F 2/4611* (2013.01); *A61F 2002/2835* (2013.01); *A61F 2002/3024* (2013.01); *A61F 2002/3042* (2013.01); *A61F 2002/3055* (2013.01); *A61F 2002/3079* (2013.01); *A61F 2002/3082* (2013.01); *A61F 2002/30171* (2013.01); *A61F 2002/30235* (2013.01); *A61F 2002/30331* (2013.01); *A61F 2002/30354* (2013.01); *A61F 2002/30362* (2013.01); *A61F 2002/30367* (2013.01); *A61F 2002/30393* (2013.01); *A61F 2002/30395* (2013.01); *A61F 2002/30405* (2013.01); *A61F 2002/30428* (2013.01); *A61F 2002/30431* (2013.01); *A61F 2002/30433* (2013.01); *A61F 2002/30434* (2013.01); *A61F 2002/30438* (2013.01); *A61F 2002/30444* (2013.01); *A61F 2002/30482* (2013.01); *A61F 2002/30504* (2013.01); *A61F 2002/30507* (2013.01); *A61F 2002/30509* (2013.01); *A61F 2002/30512* (2013.01); *A61F 2002/30523* (2013.01); *A61F 2002/30556* (2013.01); *A61F 2002/30579* (2013.01); *A61F 2002/30596* (2013.01); *A61F 2002/30598* (2013.01); *A61F 2002/30601* (2013.01); *A61F 2002/30774* (2013.01); *A61F 2002/30777* (2013.01); *A61F 2002/30779* (2013.01); *A61F 2002/30784* (2013.01); *A61F 2002/30785* (2013.01); *A61F 2002/30789* (2013.01); *A61F 2002/30818* (2013.01); *A61F 2002/30836* (2013.01); *A61F 2002/30841* (2013.01); *A61F 2002/30843* (2013.01); *A61F 2002/443* (2013.01); *A61F 2002/4475* (2013.01); *A61F 2002/4627* (2013.01); *A61F 2002/4628* (2013.01)

(58) Field of Classification Search
USPC .......................................... 623/17.11–17.16
See application file for complete search history.

(56) References Cited

U.S. PATENT DOCUMENTS

| | | |
|---|---|---|
| 6,447,518 B1 | 9/2002 | Krause et al. |
| 7,803,191 B2 | 9/2010 | Biedermann et al. |
| 2002/0082696 A1* | 6/2002 | Harms ................ A61F 2/44 623/17.11 |
| 2005/0209697 A1* | 9/2005 | Paponneau ........... A61F 2/44 623/17.15 |
| 2006/0058877 A1* | 3/2006 | Gutlin ................. A61F 2/44 623/17.11 |
| 2006/0200244 A1* | 9/2006 | Assaker ............... A61F 2/44 623/17.15 |
| 2008/0161926 A1* | 7/2008 | Melkent .............. A61F 2/44 623/17.16 |
| 2008/0167720 A1* | 7/2008 | Melkent ........... A61F 2/4637 623/17.16 |
| 2008/0177387 A1* | 7/2008 | Parimore ............. A61F 2/44 623/17.16 |
| 2008/0243254 A1* | 10/2008 | Butler ................. A61F 2/44 623/17.16 |
| 2009/0254181 A1 | 10/2009 | Boyd et al. |
| 2010/0094424 A1* | 4/2010 | Woodburn ........... A61F 2/44 623/17.16 |
| 2010/0179655 A1* | 7/2010 | Hansell ............... A61F 2/44 623/17.11 |
| 2011/0218631 A1* | 9/2011 | Woodburn, Sr. ..... A61F 2/44 623/17.16 |
| 2011/0245927 A1 | 10/2011 | Farris |
| 2011/0307065 A1 | 12/2011 | Hsu et al. |
| 2012/0101576 A1* | 4/2012 | Dewey ................ A61F 2/44 623/17.11 |
| 2012/0130493 A1* | 5/2012 | McLaughlin ..... A61F 2/4455 623/17.16 |
| 2012/0209384 A1* | 8/2012 | Arnold ............. A61F 2/4455 623/17.15 |
| 2012/0232660 A1* | 9/2012 | Davenport ........... A61F 2/44 623/17.16 |
| 2013/0006359 A1* | 1/2013 | Fedorov ............ A61F 2/4465 623/17.16 |
| 2013/0310938 A1* | 11/2013 | Sournac .............. A61F 2/44 623/17.15 |
| 2014/0107787 A1* | 4/2014 | Stinchfield .......... A61F 2/44 623/17.16 |
| 2014/0207236 A1* | 7/2014 | Prevost ............... A61F 2/44 623/17.16 |
| 2015/0066146 A1* | 3/2015 | Laubert ............. A61F 2/442 623/17.16 |

* cited by examiner

TISSUE SPACER IMPLANTS, INSERTION AND ADJUSTMENT TOOLS, AND METHOD OF USE

CROSS REFERENCE TO RELATED APPLICATIONS

This application is a National Stage application based on International Application PCT/US2013/025134 filed on Feb. 7, 2013, published as WO 2012/119803 A1 on Aug. 15, 2013. This application also claims priority benefit under 35 U.S.C. §119(e) of U.S. provisional application No. 61/595,755 filed Feb. 7, 2012, which are incorporated herein by reference.

TECHNICAL FIELD

The present invention relates generally to general surgery, orthopedic and neurosurgical implants used for insertion within a space between hard and soft tissue structures, and more specifically, but not exclusively, concerns devices implanted within a bone to replace a resected, fractured or diseased portion and to maintain or reestablish proper spacing between the bone fragments.

BACKGROUND OF THE INVENTION

Damage or disease that affects the integral structure of a bone or other structures, may lead to neurologic impairment or loss of structural support integrity with possible permanent damage to the surrounding soft tissue and adjacent neurologic, vascular and systemic structures. Maintaining or reestablishing anatomic spacing within a bone structure or other structural tissue is critical to ensuring continued functionality and mobility of the patient and avoidance of long-term serious neurological, vascular or other systemic impairments. Please note that the terms "implant" and "device" may be used interchangeably and have the same meaning herein.

SUMMARY OF THE INVENTION

Advancement of the state of tissue spacer devices and implants and the surgical management relating to the clinical presentation of missing or damaged bone fragments and other hard/soft tissue structures within the body is believed desirable. One example of an embodiment of the invention that satisfies the need for improvements to a tissue spacer device used to treat patients suffering from either diseased or damaged bone or other tissue structures includes a first cylindrical body, a second cylindrical body, an adjustment member, an end member, and a travel mechanism.

The present invention provides in one aspect, a tissue spacer implant including a first cylindrical body with an outer surface, an axially extending hole, and a first end and a second cylindrical body with an outer surface and an axially extending hole. The implant may also include an adjustment member with an outer surface, an axial hole extending from a first end to a second end, and at least one diagonal slot extending partially around the outer surface of the adjustment member. The axial hole of the adjustment member is adapted to receive the first cylindrical body and the adjustment member is configured to be inserted into the axially extending hole of the second cylindrical body. In addition, the implant may include a first travel mechanism for engaging the first cylindrical body, the adjustment member, and the second cylindrical body along the at least one diagonal slot of the adjustment member to maintain a space between two bodies of tissue.

The present invention provides in another aspect, a tissue spacer implant including at least one inner cylindrical body with an outer surface, an axially extending hole, and a first end and an outer cylindrical body with an outer surface and an axially extending hole. The implant may also include at least one adjustment member with an outer surface, an axially extending hole, and at least one helical slot around the outer surface of the at least one adjustment member. The axially extending hole of the at least one adjustment member is adapted to receive the outer surface of the at least one inner cylindrical body and the outer surface of the at least one adjustment member is adapted to be inserted into the axially extending hole of the outer cylindrical body. In addition, the implant may include at least one travel mechanism. The at least one travel mechanism may include a shaft, the shaft may pass through the at least one inner cylindrical body, the at least one adjustment member, and the outer cylindrical body to maintain a desired position along the at least one helical slot of the at least one adjustment member.

The present invention provides in yet another aspect, a surgical method for maintaining a space between two tissue bodies in a living being. The method may include the step of obtaining a medical device that has a first cylindrical body that includes an outer surface, an axially extending hole, and a first end. The medical device includes a second cylindrical body with an outer surface and an axially extending hole. The medical device also includes an adjustment member with an outer surface, an axial hole extending from a first end to a second end, and at least one helical slot extending partially around the outer surface of the adjustment member. The axial hole of the adjustment member is adapted to receive the first cylindrical body and the adjustment member is configured to be inserted into the axially extending hole of the second cylindrical body. In addition, the medical device may also include a first travel mechanism engaging the first cylindrical body, the adjustment member, and the second cylindrical body along the at least one helical slot of the adjustment member to maintain a space between two bodies of tissue. The method may further include the step of coupling the second cylindrical body of the medical device to a tool. The method may also include the step of positioning and inserting the tool with the medical device in a retracted position into a space between the two tissue bodies to maintain or increase the space therebetween. The method may also include the further step of adjusting the medical device along the at least one helical slot of the adjustment member to a desired length. The method typically further includes the step of securing the first cylindrical body, the adjustment member, and the second cylindrical body using a locking mechanism at a desired length.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which:

DETAILED DESCRIPTION FOR CARRYING OUT THE INVENTION

Generally stated, disclosed herein are tissue spacer implants, an adjustment tool, and an insertion tool. As used herein, the terms "tissue spacer implant," "implant," "medical device," and "device" may be used interchangeably as they essentially describe the same type of device. Surgical methods for implanting the tissue spacer implants are also disclosed.

Figure 1:
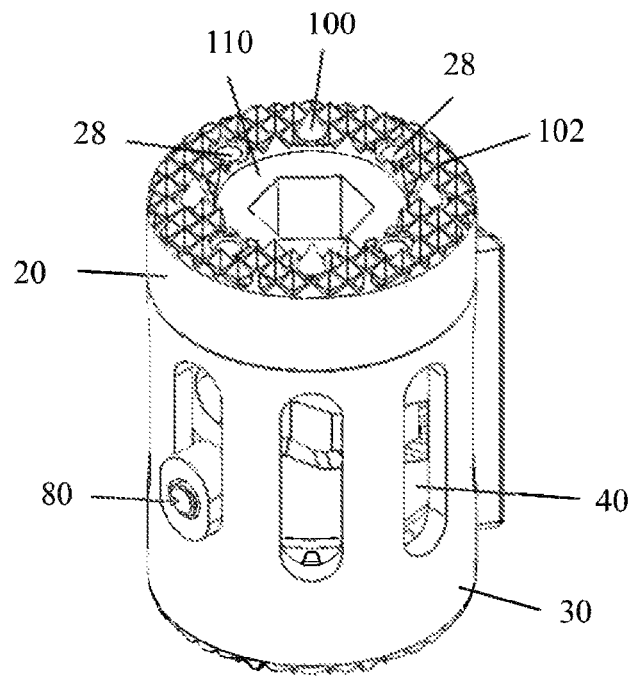
FIG. 1 is a perspective view of one embodiment of a tissue spacer device in a refracted position, in accordance with an aspect of the present invention.

As shown in FIG. 1, the general arrangement of a tissue spacer implant 10, in accordance with an aspect of the present invention, may include a cylindrical body or post-like member. The implant 10 as shown in FIGS. 1-6 has, for example, a generally circular cross-sectional geometry, although it is contemplated that other geometric or anatomical shapes may also be used in the construct. The implant 10 may likely include an end member 20, an outer cylindrical body 30, an intermediate adjustment member 40, and an inner cylindrical body 50. The implant 10 may also include a fastener 110. The intermediate adjustment member 40 is detachably coupled to the inner cylindrical body or first cylindrical body 50 and the outer cylindrical body or second cylindrical body 30. The terms "inner cylindrical body" and "first cylindrical body" may be used interchangeably as they have essentially the same meaning herein. Likewise, the terms "outer cylindrical body" and "second cylindrical body" may be used interchangeably as they have essentially the same meaning herein. In addition, the terms "intermediate adjustment member" and "adjustment member" may be used interchangeably as they have essentially the same meaning herein. The end member 20 is detachably coupled to the inner cylindrical body 50 and the fastener 110 may be used to detachably couple the end member 20 to the inner cylindrical body 50.

Figure 10:
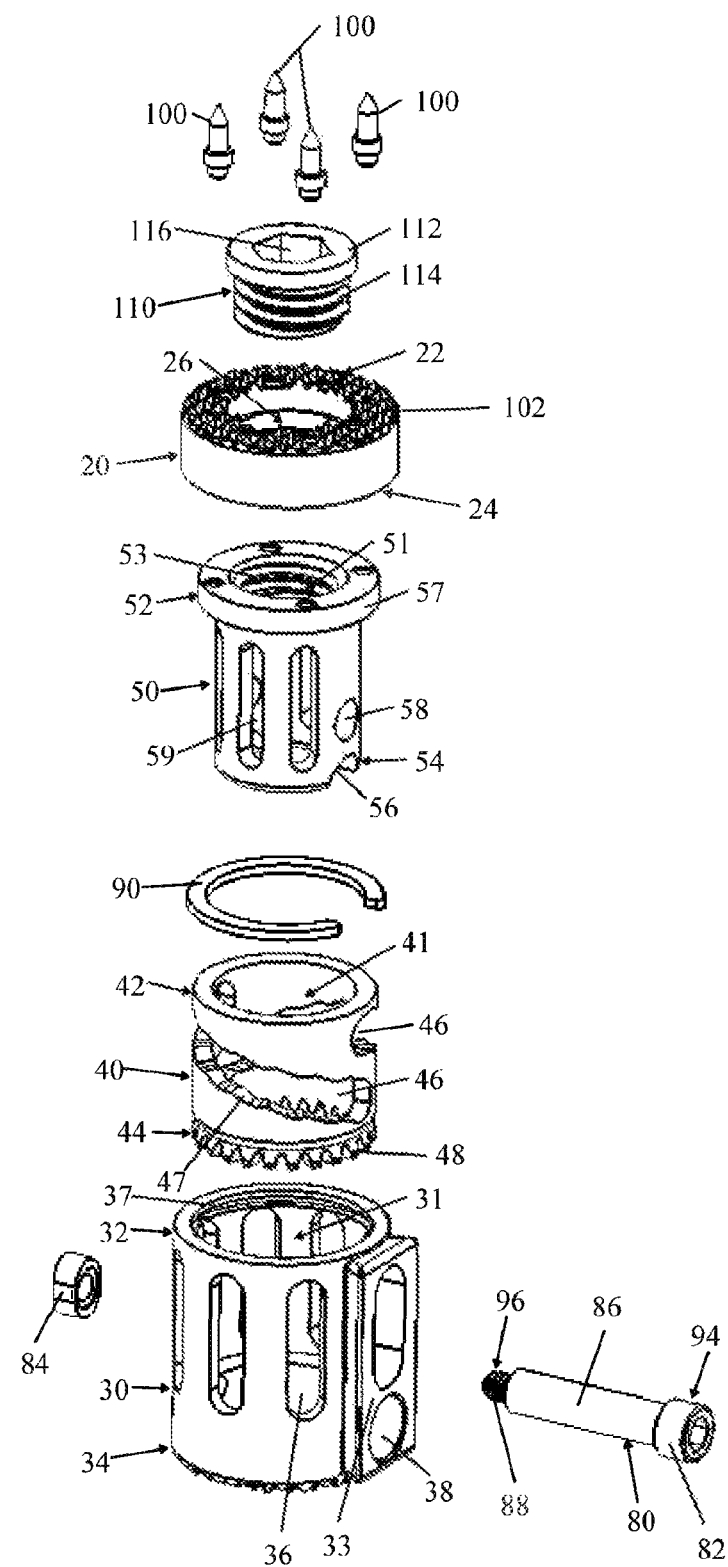
FIG. 10 is a fully exploded side, perspective view of the tissue spacer device of FIG. 1, in accordance with an aspect of the present invention.
Figure 11:
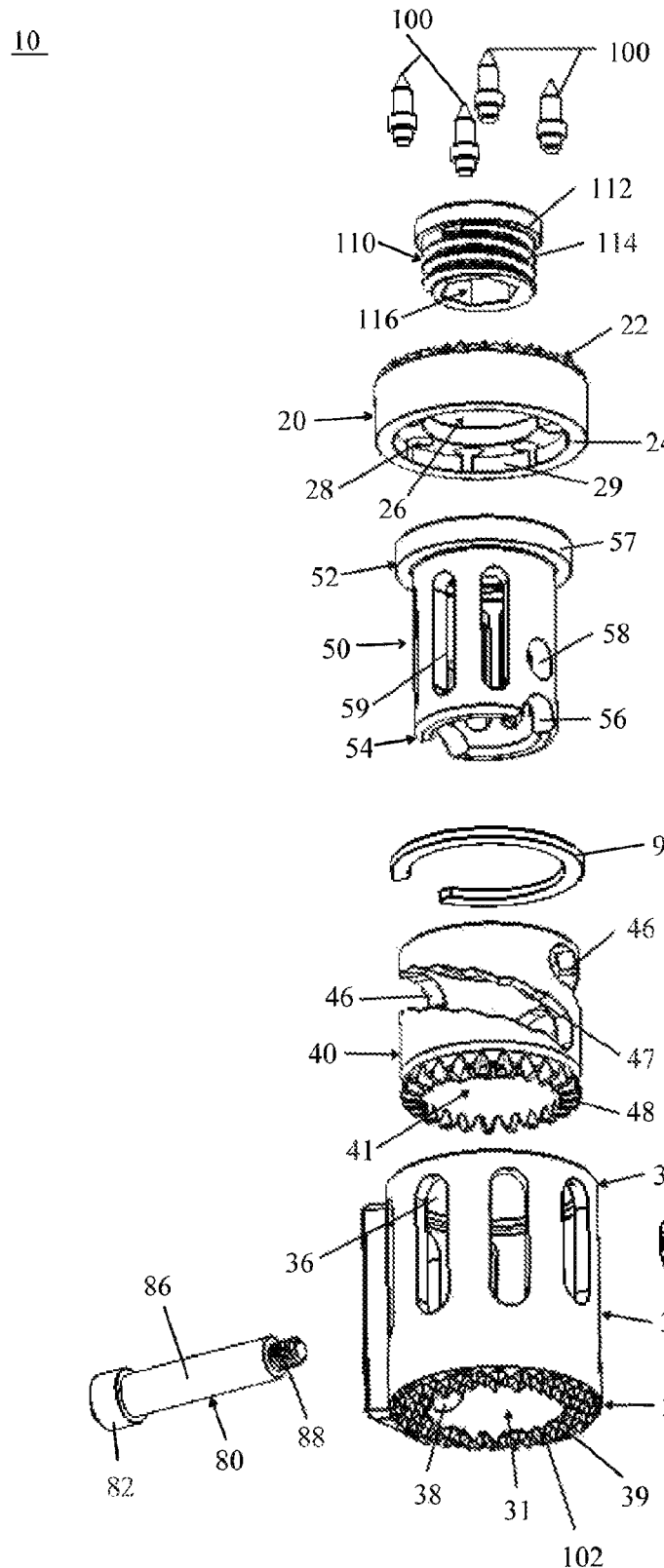
FIG. 11 is a fully exploded back, perspective view of the tissue spacer device of FIG. 1, in accordance with an aspect of the present invention.
Figure 13:
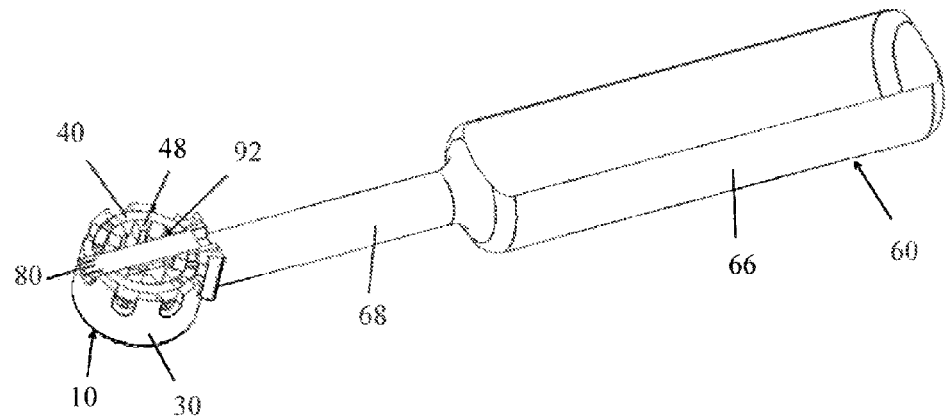
FIG. 13 is a cross sectional view of the device shown in FIG. 3 as viewed along section line 13-13 in FIG. 3, in accordance with an aspect of the present invention.
Figure 14:
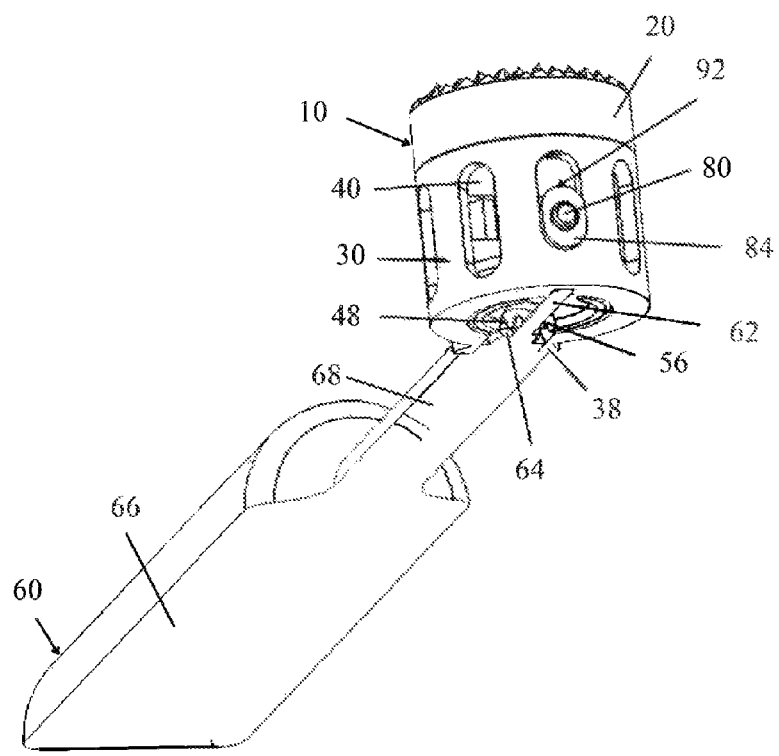
FIG. 14 is a cross sectional view of the device shown in FIG. 3 as viewed along section line 14-14 in FIG. 3, in accordance with an aspect of the present invention.

As seen in FIGS. 10-11, the end member 20 typically includes a first end 22 and second end 24, the outer cylindrical body 30 typically includes a first end 32 and second end 34, the intermediate adjustment member 40 typically includes a first or superior end 42 and second or inferior end 44, and the inner cylindrical body 50 typically includes a first end 52 and second end 54. The first end 22 of the end member 20 being configured to provide a bone contacting surface and the second end 24 being configured to couple to the first end 52 of the inner cylindrical body 50. The fastener 110 may be used to secure the end member 20 to the inner cylindrical body 50. The second end 54 of the inner cylindrical body 50 may be configured to couple to the first end 42 of the intermediate adjustment member 40. The second end 44 of the intermediate adjustment member 40 may be configured to couple with the first end 32 of the outer cylindrical body 30 and for mating with a tool, for example, adjustment mechanism 60 or the positioning mechanism 440 of the insertion tool 400. The terms "adjustment mechanism," "tool," "adjustment tool," and "instrument" may be used interchangeably herein as they essentially refer to the same device. The second end 34 of the outer cylindrical body 30 may be configured to provide a bone contacting surface 102. As shown in FIGS. 13-14, the outer cylindrical body 30, intermediate adjustment member 40, and inner cylindrical body 50 may, for example, have a circular cross sectional shape, but other polygonal or anatomical shapes may be used.

Figure 2:
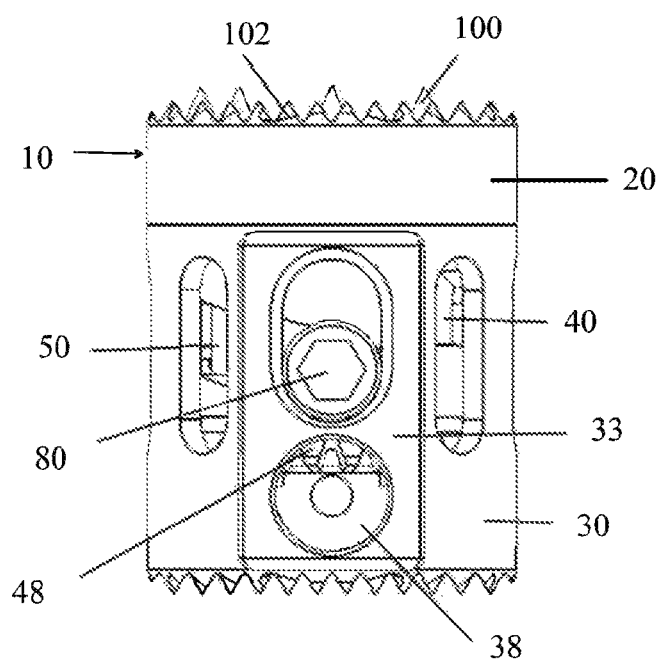
FIG. 2 is a front view of the tissue spacer device of FIG. 1, in accordance with an aspect of the present invention.
Figure 3:
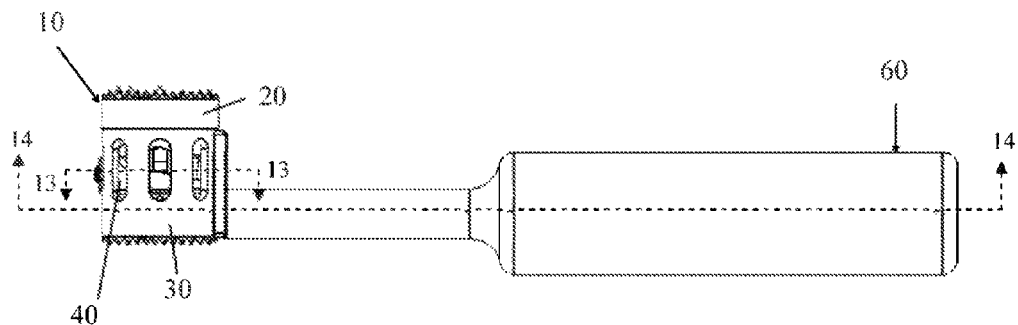
FIG. 3 is a side view of the tissue spacer device of FIG. 1 with a tool inserted into the tissue spacer device, in accordance with an aspect of the present invention.
Figure 4:
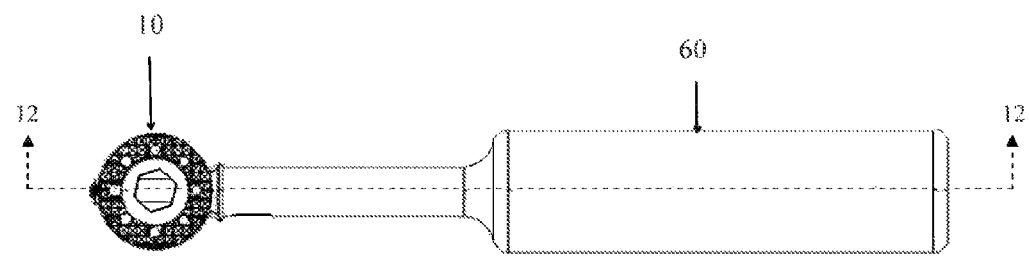
FIG. 4 is a top view of the tissue spacer device of FIG. 1 and the tool of FIG. 3, in accordance with an aspect of the present invention.
Figure 5:
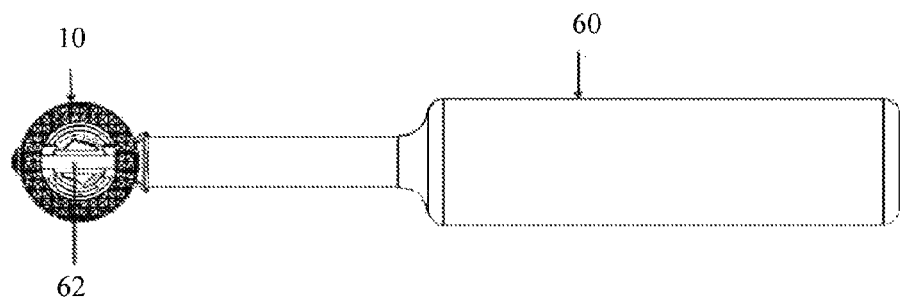
FIG. 5 is a bottom view of the tissue spacer device of FIG. 1 and the tool of FIG. 3, in accordance with an aspect of the present invention.

The end member 20 may also be hollow or include a central bore 26 that passes from the first end 22 to the second end 24. The central bore 26 may be filled with bone graft material post-implantation. The first end 22 may include a ridged contact surface with a plurality of openings 28, as seen in FIGS. 1 and 4, the disclosed embodiment includes, for example, eight openings, which may be threaded. As best seen in FIG. 1, one or more threaded spikes 100 may be inserted into the plurality of openings 28. The threaded spikes 100 may be used to fasten the end member 20 to the inner cylindrical body 50, as well as to provide additional contact with the adjacent vertebral body. It should be understood by one skilled in the art that it is contemplated that modular end surfaces or end members 20 may be used to provide for varying types of bone contacting surfaces and structures, including, but not limited to sharp tines, porous coatings, biomaterial/ingrowth surfaces, and teeth-like structures. End member 20 may also include teeth-like structures 102 as depicted in FIGS. 1-3. Although not shown, it is also understood that alternative modular end surfaces or angled end surfaces may be attached to the end member 20 using many different coupling mechanisms including, but not limited to, snap locks, screws, pins, etc., to address various clinical deformities. The end member 20 also includes a second end 24 including an inner ring 29 that mates with the rim 57 on the first end 52 of the inner cylindrical body 50. As shown, the end member 20 has a generally circular cross-sectional geometry, although it is contemplated that various cross-sectional geometries could be used in the construct depending upon the anatomic situation and clinical application.

Figure 9:
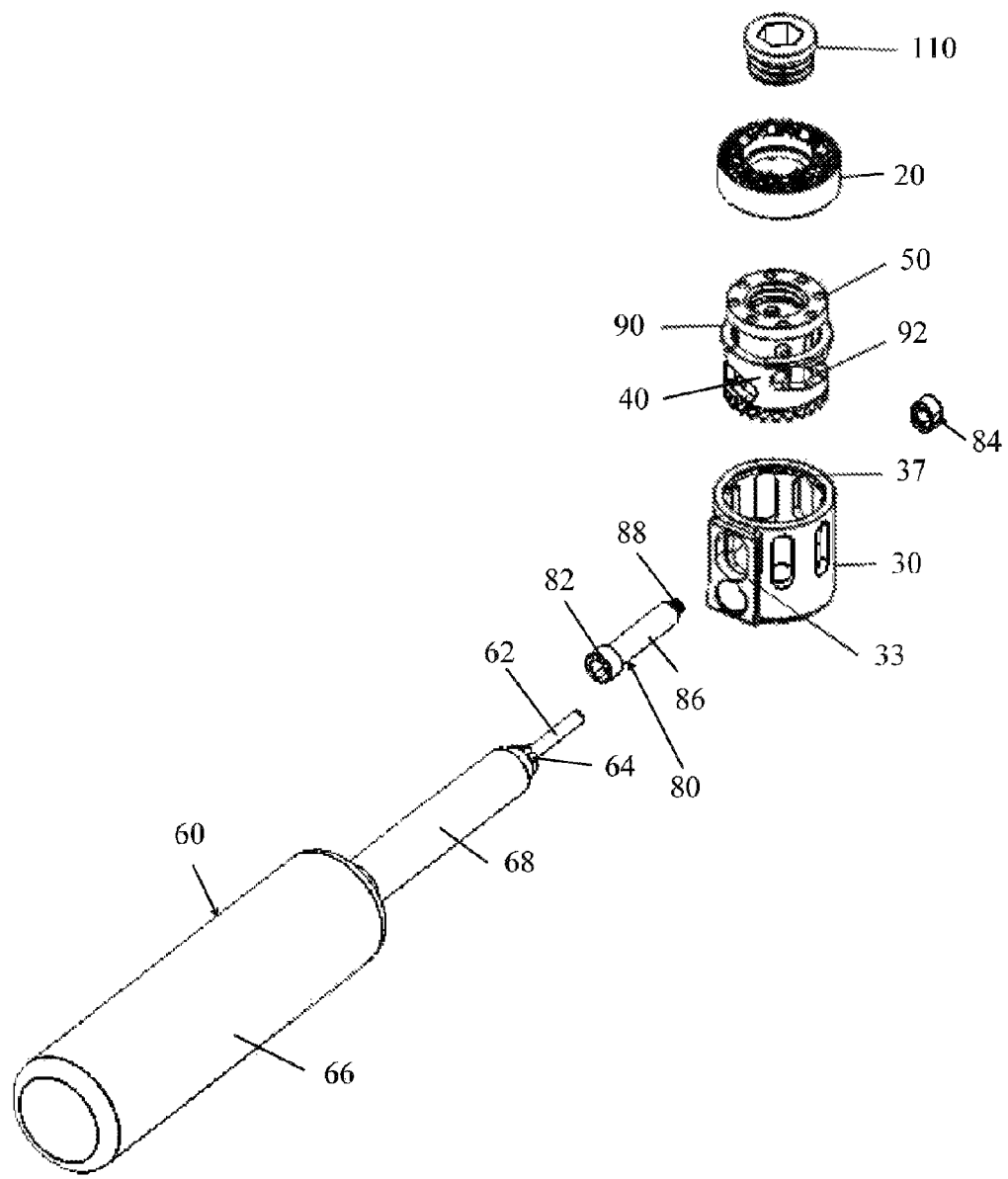
FIG. 9 is a partially exploded perspective view of the tissue spacer device of FIG. 1 and the tool of FIG. 3, in accordance with an aspect of the present invention.

As seen in FIGS. 9-11, the inner cylindrical body 50 may include a rim 57 or teeth-like structures (not shown) around the first end 52 for mating with end member 20. The inner cylindrical body 50 also has parallel cutouts 56 in the second end 54 to provide clearance for a tool, for example, the adjustment tool 60 or positioning mechanism 440 of the insertion tool 400, when it is inserted into the implant 10. In the depicted embodiment of FIGS. 10-11, the cutouts 56 are configured as half circles, although many other geometric shapes are contemplated and the shapes shown here are for example purposes only. Above the cutouts 56 are two parallel holes or openings 58 which may mate with the travel mechanism 80 to secure the intermediate adjustment member 40 at a desired separation. Also along the inner cylindrical body 50 between the first end 52 and the second end 54 there may be a plurality of elongated vertically oriented openings 59 passing through the outer surface into the central cavity 51. The elongated vertically oriented openings 59 may be oval in shape, as seen in FIGS. 10 and 11, although many other geometric shapes are contemplated and the shapes shown are for example purposes only. The first end 52 of the central cavity may include interior threads 53 for engaging the threaded end 114 of the fastener 110, as seen in FIG. 10.

As shown in FIGS. 9-11, the intermediate adjustment member 40 may include two diagonal or helical openings 46 between the first end 42 and the second end 44 passing through the outer surface into the central cavity 41. The diagonal openings 46 are angled from the first end 42 towards the second end 44, although other alignment angles are contemplated. As seen in FIGS. 10 and 11, the openings 46 are slots, although many other geometric shapes are contemplated and the shapes shown are for example purposes only. The openings 46 may include depressions 47 along the inside of the openings 46 to provide indents for the shaft 86 of the travel mechanism 80 to sit in at the various adjustment heights. However, the openings 46 may also have smooth walls with any incremental changes of height being controlled and determined by the spacing of the gears 48 on the adjustment member 40. The second end 44 of the intermediate adjustment member 40 may include teeth-like or gear structures 48 for mating with a tool, for example, the adjustment tool 60 or insertion tool 400.

Figure 12:
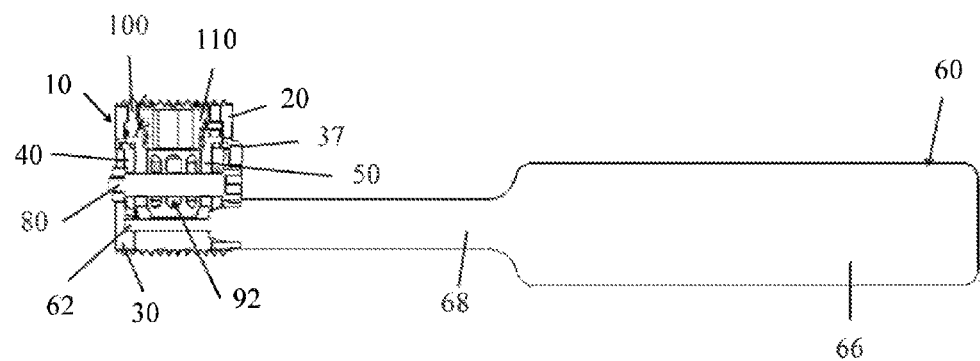
FIG. 12 is a cross sectional view of the device shown in FIG. 4 as viewed along section line 12-12 in FIG. 4, in accordance with an aspect of the present invention.

Continuing to refer to FIGS. 9-11, the outer cylindrical body 30 may include a plurality of vertical or oblong openings 36 along the outer surface that extend between the first end 32 and the second end 34 passing through the outer surface and into the central cavity 31. The vertical openings 36 as seen in FIGS. 10 and 11, may be oval in shape, although many other geometric shapes are contemplated and the shapes shown are for example purposes only. At least one of the plurality of vertical openings 36 may be shorter than the remaining plurality of vertical openings 36 where the adjustment opening 38 is located near the second end 34 of the outer cylindrical body 30. The adjustment opening 38 and shorter vertical opening 36 extend from the central cavity 31 to the exterior of the cylindrical body 30 through an engagement boss 33. The engagement boss 33 extends out from the exterior surface of the cylindrical body 30 at an angle to create a surface for a tool, for example, insertion tool 400, to engage the implant 10 during insertion and adjustment in the patient. The bottom surface 39 of the second end 34 being configured to provide a bone contacting surface and having a ridged contact surface. It should be understood by one skilled in the art that it is contemplated that the second end 34 of the outer cylindrical body 30 may have varying types of bone contacting surfaces and structures, including, but not limited to sharp tines, porous coatings, biomaterial/ingrowth surfaces, and teeth-like structures 102, as seen in FIGS. 1, 2, 10 and 11. The outer cylindrical body 30 may also include an interior rim 35, as shown in FIGS. 10 and 12. The interior rim 35 may have a gap where the interior rim 35 intersects with the adjustment opening 38 to enable an adjustment mechanism or tool to be inserted into the adjustment opening 38. The interior rim 35 engages the second end 44 of the intermediate adjustment member 40 and maintains the intermediate adjustment member 40 between the interior rim 35 and the support means 90 within the outer cylindrical body 30. The outer cylindrical bodies 230 and 330, described in greater detail below, may also include at least one interior rim, such as interior rim 35, to maintain the intermediate adjustment members 240, 340 within the outer cylindrical bodies 230 and 330.

As seen in the exploded view of FIG. 9, the intermediate adjustment member 40 is positioned above the inner cylindrical body 50. A support means 90, for example, a washer may be positioned adjacent the first end 52 of the inner cylindrical body 50 prior to inserting the intermediate adjustment member 40 over the second end 54 and the body 50. The end member 20 may then be secured to the inner cylindrical body 50 using the fastener 110. As seen in FIGS. 9 and 12 the outer cylindrical body 30 may then be positioned over the intermediate adjustment member 40 and the support member 90 may be inserted into the channel 37 in the outer cylindrical body 30.

Figures 38, 39:
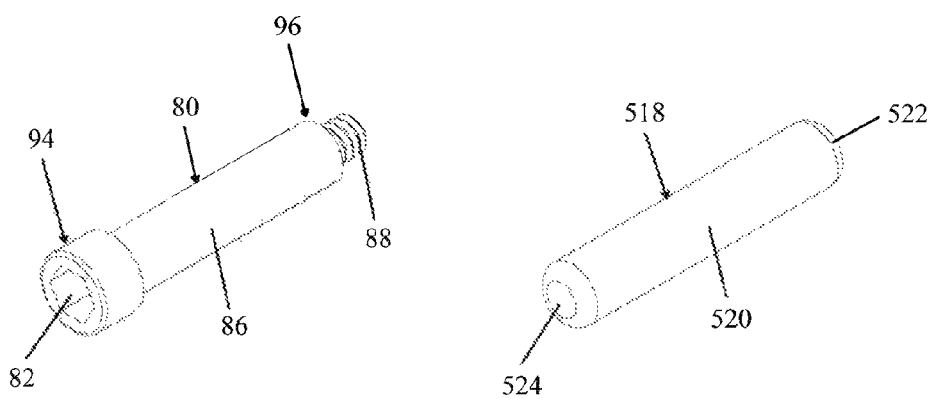
FIG. 38 is a perspective view of a travel mechanism for a tissue spacer implant, in accordance with an aspect of the present invention.
FIG. 39 is a perspective view of another travel mechanism for a tissue spacer implant, in accordance with an aspect of the present invention.

As seen in the sectional views of FIGS. 12-14, a channel 92 is created by the combination of two parallel vertical openings 36 of the outer cylindrical body 30 being aligned with the openings 46 of the adjustment member 40 and the two parallel holes 58 of the inner cylindrical member 50. A shaft 86 of the travel mechanism 80 may be inserted into the channel 92. As shown in FIG. 38, the shaft 86 may include a first end 94 and a second end 96. The first end 94 may, for example, include a head portion 82 and the second end 96 may, for example, include a threaded portion 88. The head portion 82 of the travel mechanism 80 may mate with one of the parallel vertical openings 36 of the outer cylindrical body 30 and the threaded portion 88 exiting the parallel opening 36 of the body 30. The threaded portion 88 may mate with an engagement member 84, such as a nut. An optional washer (not shown) may be inserted over the second end 96 prior to attaching the engagement member 84 onto the fastener 82. The engagement member 84 may be attached to the threaded portion 88 of the travel mechanism 80 to couple the outer cylindrical body 30, the intermediate adjustment member 40, and the inner cylindrical body 50. The engagement member 84 may not be fully tightened to allow for rotation of the intermediate adjustment member 40. Once the implant 10 is at a desired height, the engagement end 84 and head portion 82 of the travel mechanism 80 may be tightened together to secure the intermediate adjustment member 40 in position and with the inner cylindrical body 50 at the selected height. Alternative means for securing the outer cylindrical body 30, the intermediate adjustment member 40, and the inner cylindrical body 50 at a desired height are discussed in greater detail below.

Figure 6:
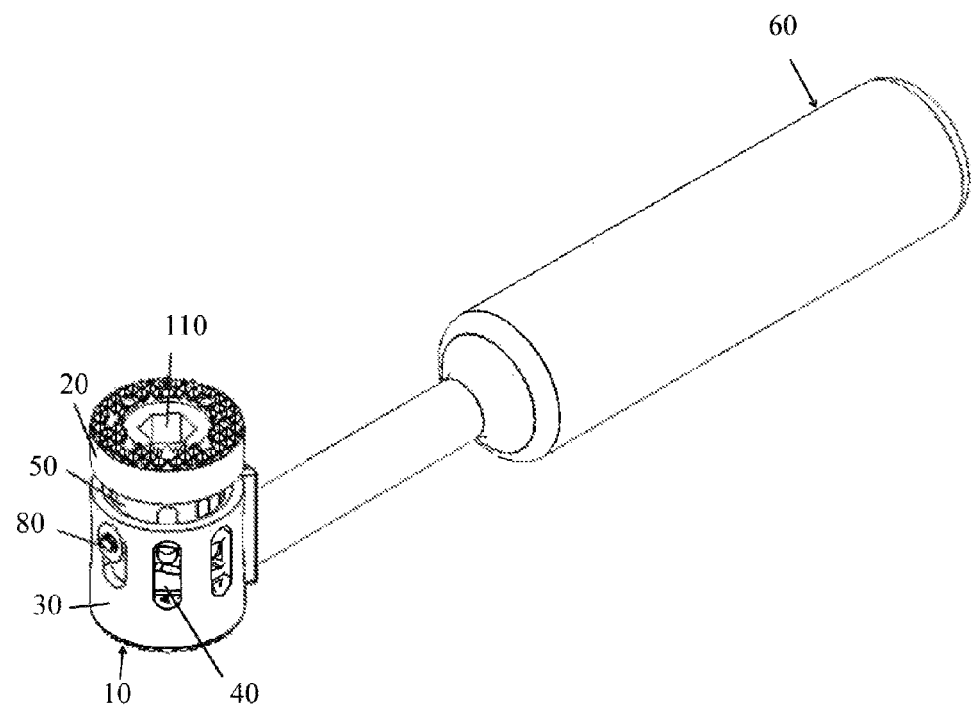
FIG. 6 is a perspective view of the tissue spacer device of FIG. 1 in a fully extended position and the tool of FIG. 3, in accordance with an aspect of the present invention.
Figure 7:
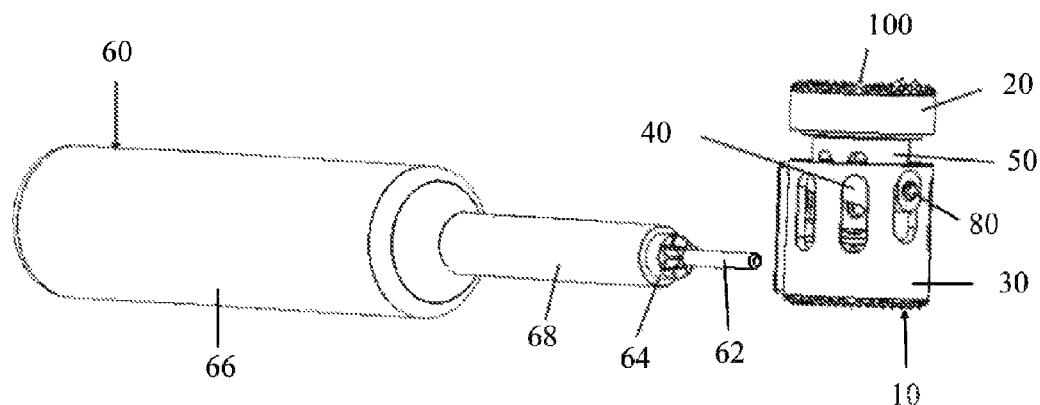
FIG. 7 is a partially exploded side, perspective view of the tissue spacer device of FIG. 1 and the tool of FIG. 3, in accordance with an aspect of the present invention.
Figure 8:
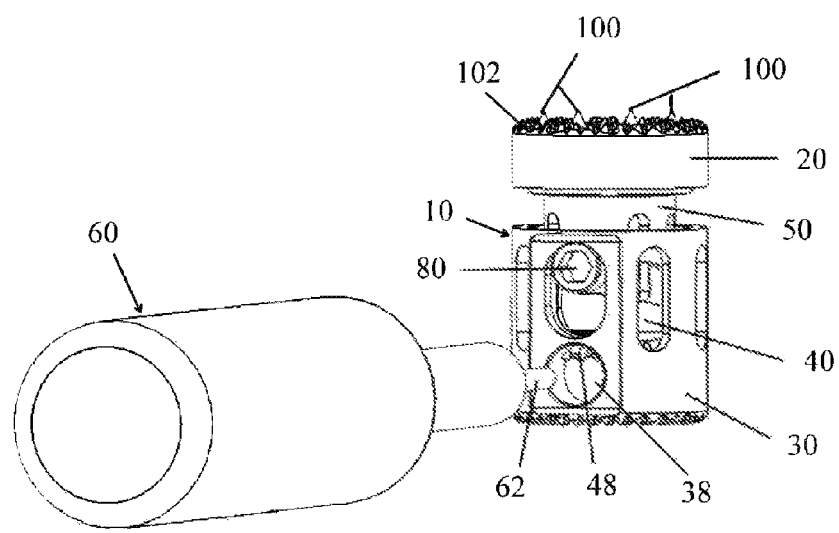
FIG. 8 is a partially exploded front, perspective view of the tissue spacer device of FIG. 1 and the tool of FIG. 3, in accordance with an aspect of the present invention.
Figure 32:
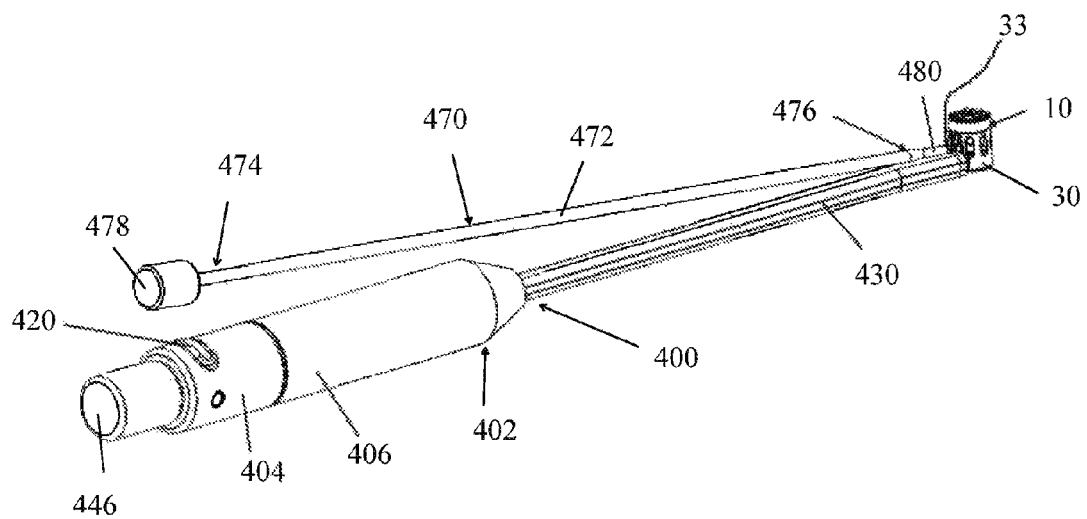
FIG. 32 is a perspective view of an insertion tool and locking instrument engaging the tissue spacer device of FIG. 1, in accordance with an aspect of the present invention.

As seen in FIGS. 1 and 6, respectively, the implant 10 is in the fully retracted position and fully extended position. In order to adjust the height of the implant 10, a tool, for example, an adjustment tool 60 or positioning mechanism 440 of the insertion tool 400, may be inserted into opening 38, as shown in FIGS. 8 and 32. The adjustment tool 60 may include a guide pin 62, a plurality of gear teeth 64, a handle 66 and a connector rod 68, as shown in FIGS. 7 and 9. The connector rod 68 is located intermediate and connects the guide pin 62 and the handle 66. The gear teeth 64 being located at the point where the connector rod 68 meets the guide pin 62. The insertion tool 400 is described in greater detail below.

As seen in FIG. 14, when the guide pin 62 is inserted into opening 38, it passes under the adjustment member 40 and the cutouts 56 of the inner cylindrical body 50. Once the adjustment tool 60 is completely inserted into the opening 38, the gear teeth 64 of the adjustment tool 60 interface with the teeth-like or gear structures 48 of the adjustment member 40. As the handle 66 is rotated the gear teeth 64 mate with the teeth-like or gear structures 48 to rotate the intermediate adjustment member 40. As the intermediate adjustment member 40 turns it causes the fixed travel mechanism 80 to slide along the path of the diagonal openings 46. Since the travel mechanism 80 is coupled to the inner cylindrical body 50, as the travel mechanism 80 moves along the diagonal slots 46 the inner cylindrical body 50 moves either upward or downward depending on the direction of rotation. The end member 20 may move away or move towards the first end 32 of the outer body 30 either lengthening or shortening the height of the implant 10, as seen in FIGS. 6-8.

Referring now to FIGS. 15-22, an alternative embodiment implant 200, similar to the implant 10 as described above, but includes a second fastener 210 and a second end member 220. The first end member 20, outer cylindrical body 230, intermediate adjustment member 240, inner cylindrical body 250, travel mechanism 80, washer 90, and fastener 110 are similar to those described above with reference to FIGS.

Figure 16:
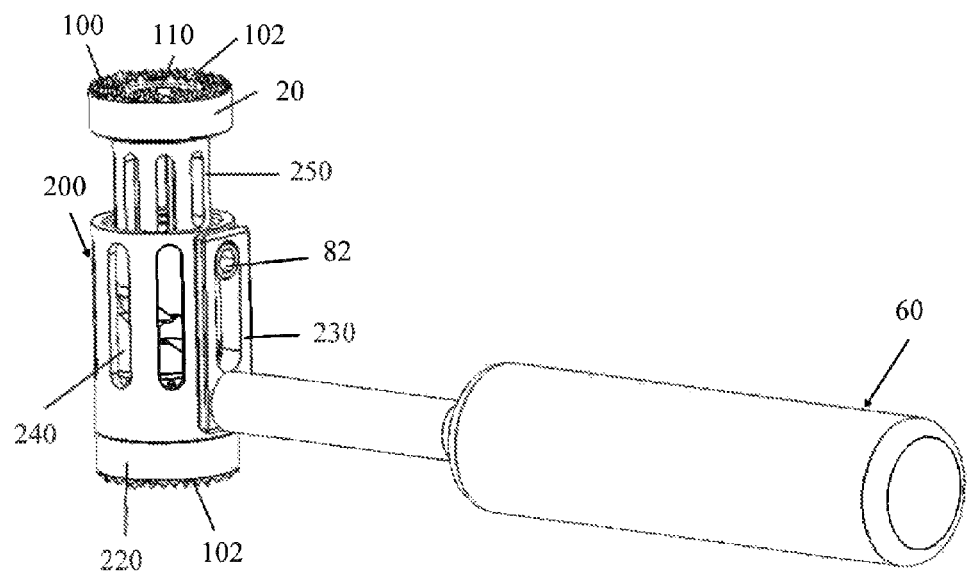
FIG. 16 is a perspective view of the tissue spacer device of FIG. 15 in a fully expanded position and the tool of FIG. 15, in accordance with an aspect of the present invention.
Figure 17:
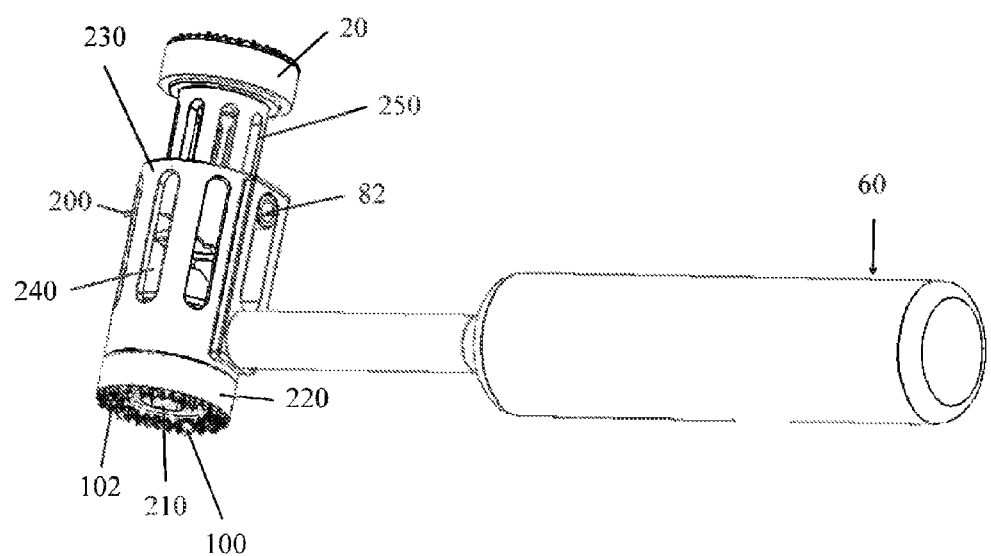
FIG. 17 is a bottom perspective view of the tissue spacer device of FIG. 15 in a fully expanded position and the tool of FIG. 15, in accordance with an aspect of the present invention.
Figure 18:
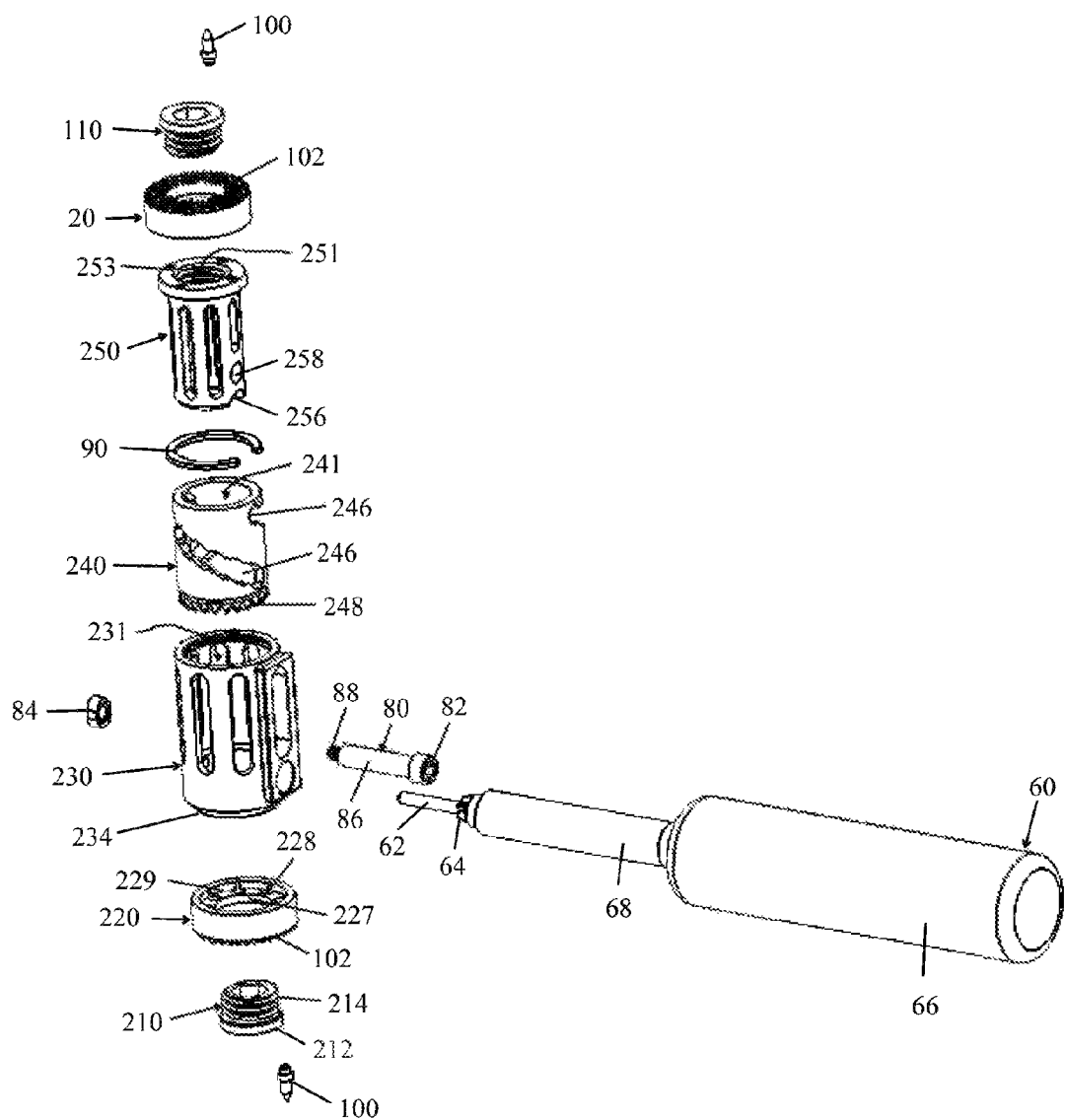
FIG. 18 is a fully exploded top perspective view of the tissue spacer device and tool of FIG. 15, in accordance with an aspect of the present invention.
Figure 19:
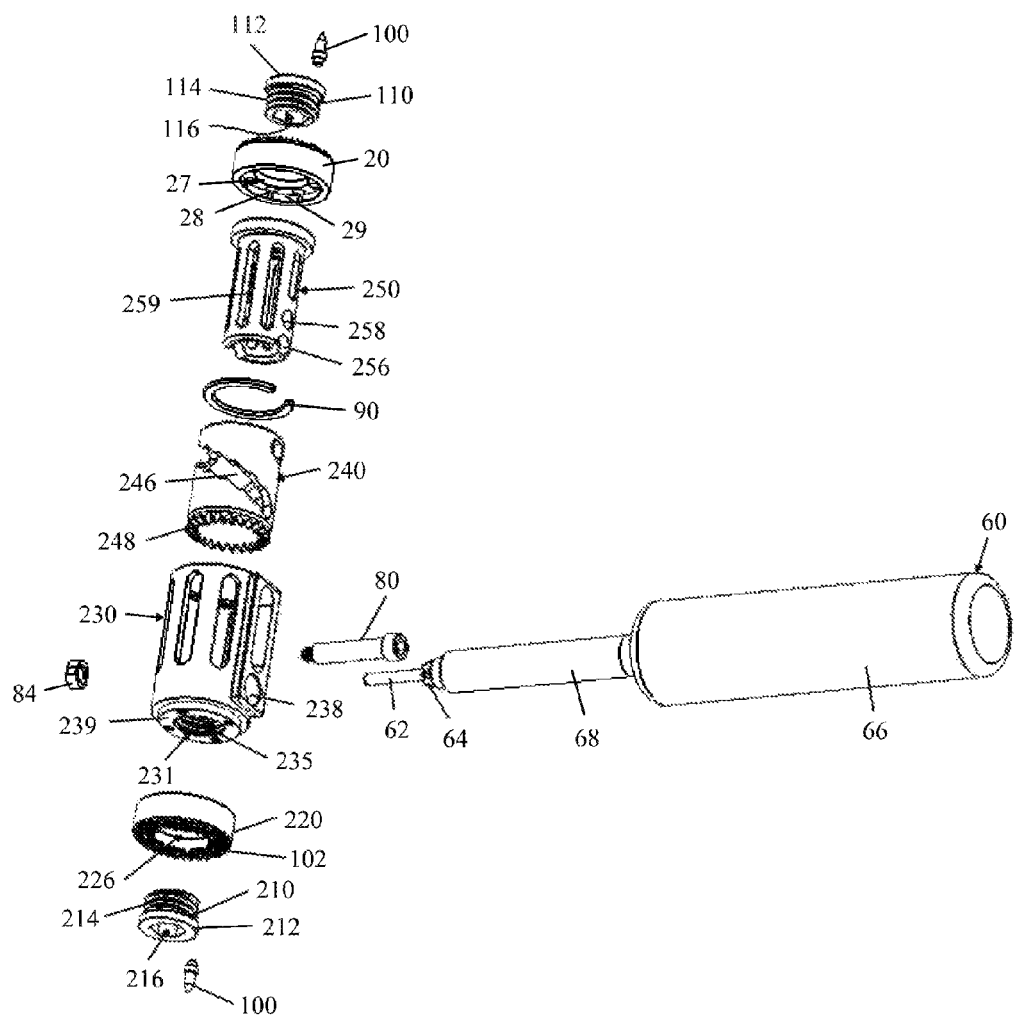
FIG. 19 is a fully exploded bottom perspective view of the tissue spacer device and tool of FIG. 15, in accordance with an aspect of the present invention.
Figure 20:
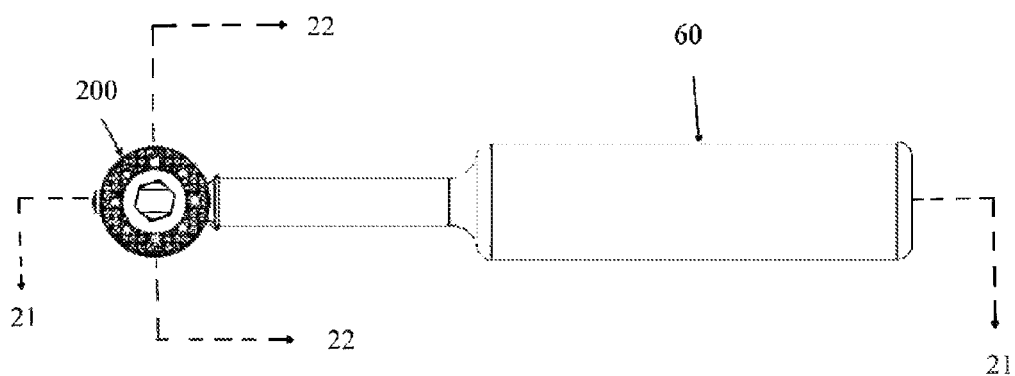
FIG. 20 is a top view of the tissue spacer device and the tool of FIG. 15, in accordance with an aspect of the present invention.
Figure 21:
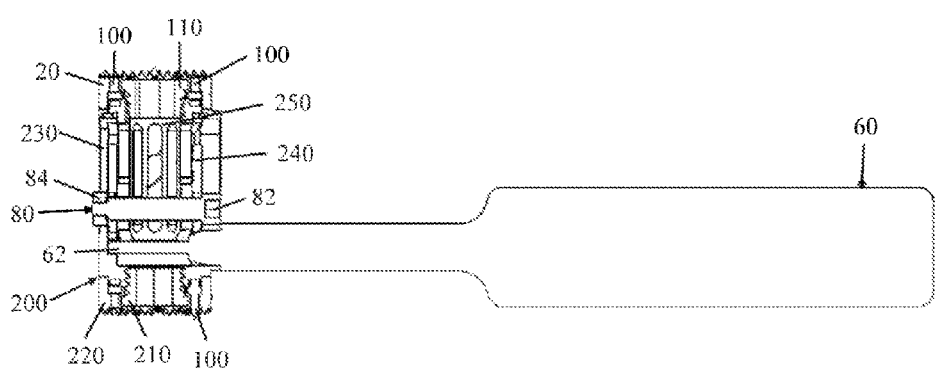
FIG. 21 is a cross sectional view of the device shown in FIG. 15 as viewed along section lines 21-21 in FIG. 20, in accordance with an aspect of the present invention.
Figure 22:
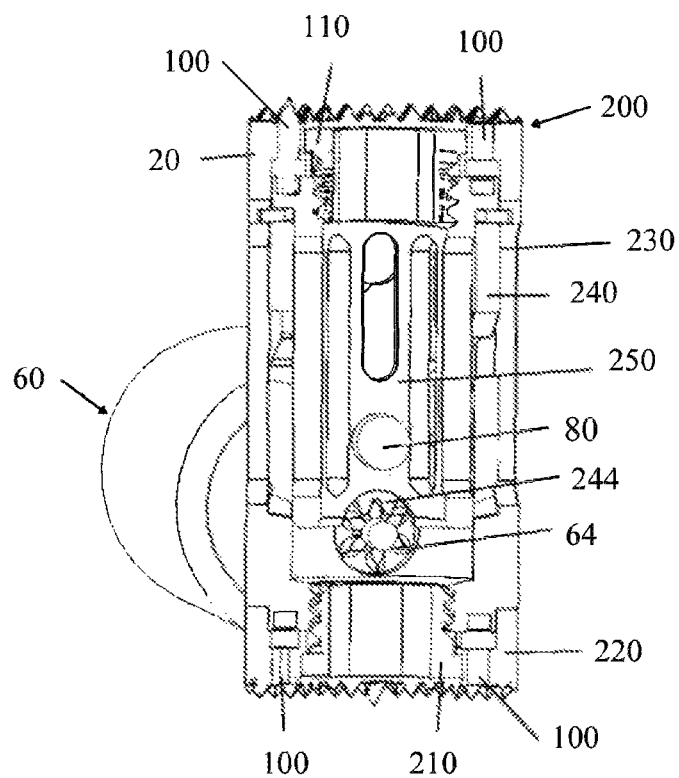
FIG. 22 is a cross sectional view of the device shown in FIG. 15 as viewed along section lines 22-22 in FIG. 20, in accordance with an aspect of the present invention.

1-14. As seen in FIG. 16, the intermediate adjustment member 240 is detachably coupled to the inner cylindrical body or first cylindrical body 250 and the elongated outer cylindrical body or second cylindrical body 230, as described above with reference to FIGS. 1-14. The first end member 20 may be detachably coupled to the inner cylindrical body 250 with the fastener 110 and the second end member 220 may be detachably coupled to the elongated outer cylindrical body 230 with a second fastener 210. The first and second end members 20, 220 each having at least one threaded spike 100 and teeth-like structures 102 on the bone contact surface for engagement with the patient's bone, as shown in FIGS. 16-18. The adjustment tool 60 is of the type described above with reference to implant 10. For brevity sake the functionality and element relationships will not be restated here, but it is understood that they include all of the same limitations of and function in the same manner as implant 10, other than addition of the second end member 220.

Figure 15:
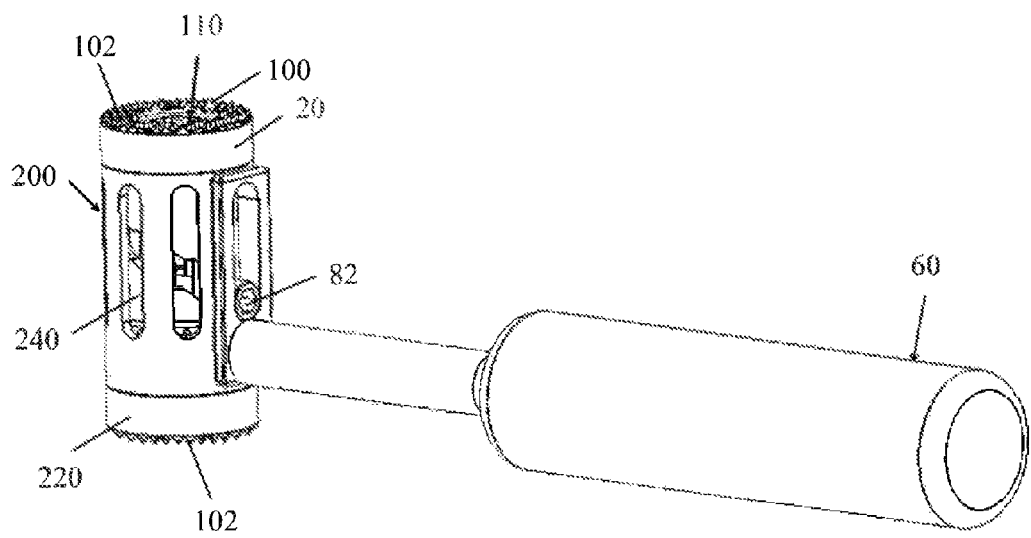
FIG. 15 is a perspective view of another alternative embodiment of a tissue spacer device in a retracted position with a tool inserted into the tissue spacer device, in accordance with an aspect of the present invention.
Figure 23:
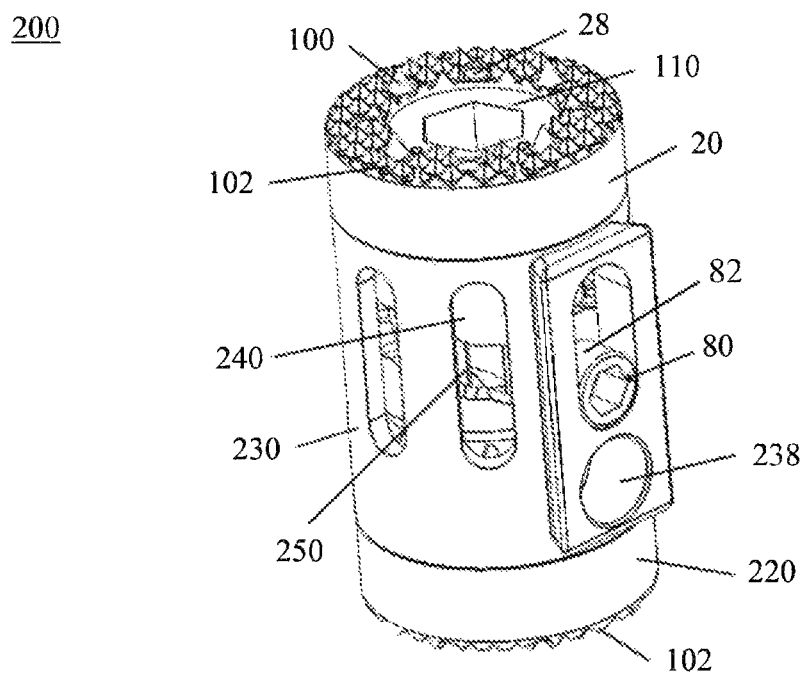
FIG. 23 is a perspective view of yet another alternative embodiment of a tissue spacer device in a retracted position, in accordance with an aspect of the present invention.
Figure 24:
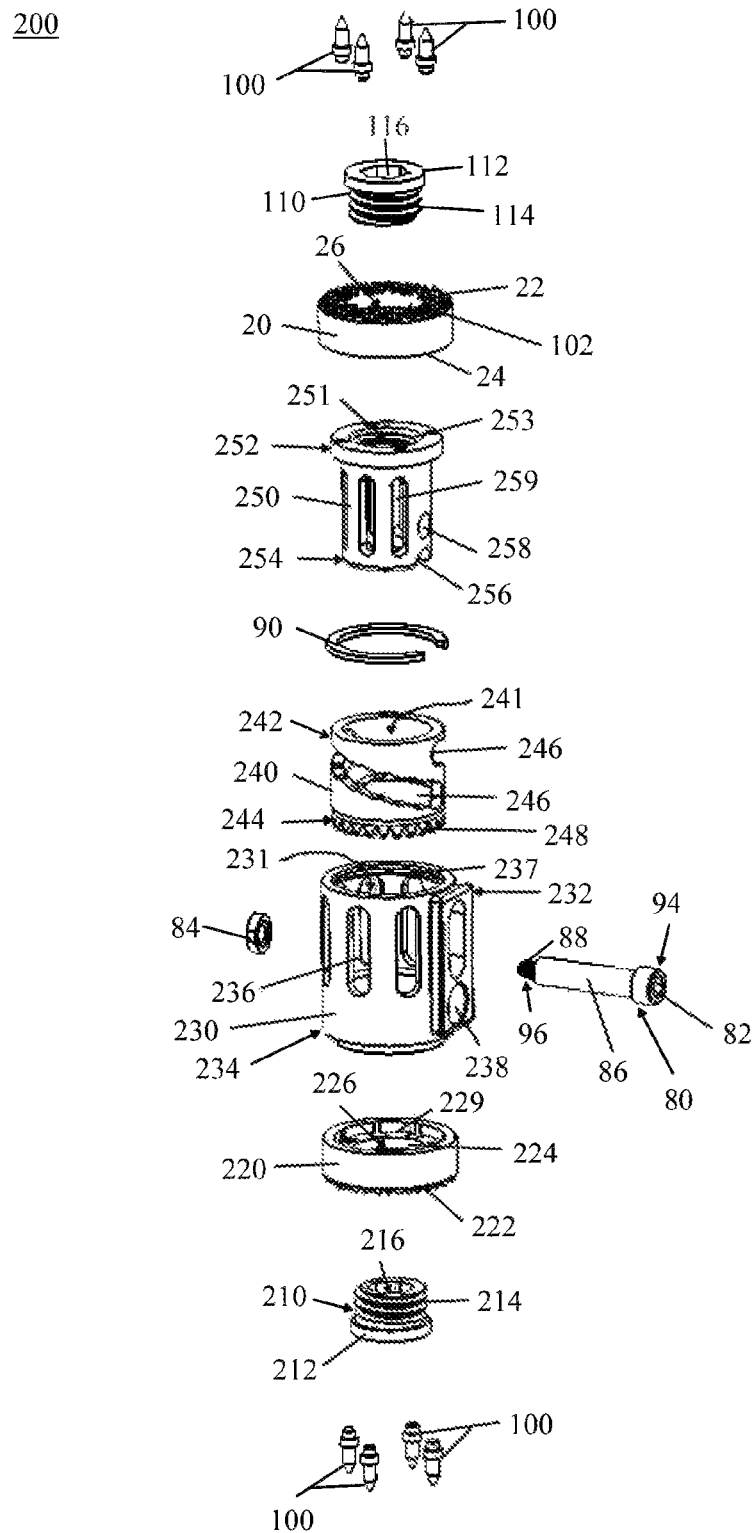
FIG. 24 is a fully exploded top perspective view of the tissue spacer device of FIG. 23, in accordance with an aspect of the present invention.

As seen in FIGS. 15 and 16, respectively, the implant 200 is in the fully retracted position and fully extended position and is adjusted as described above with reference to FIGS. 1-14. The implant 200 may come in a variety of sizes, wherein the diameter and length of the outer cylindrical body 230, intermediate adjustment member 240, and inner cylindrical body 250 vary depending on the size of the desired implant. As shown in FIGS. 15-19, for example, the outer cylindrical body 230, intermediate adjustment member 240, and inner cylindrical body 250 may be elongated. Referring now to FIGS. 23-24, the outer cylindrical body 230, intermediate adjustment member 240, and inner cylindrical body 250 may be shorter in length, thus the height of the implant 200 shown in FIGS. 23 and 24 is less than the height of the implant 200 shown in FIGS. 15-22.

Another alternative embodiment implant 300 is depicted in FIGS. 25-31, the implant 300 including an elongated outer cylindrical body or second cylindrical body 330 to accommodate a first or superior inner cylindrical body 250 and second or inferior inner cylindrical body 350 coupled to a first and second intermediate adjustment member 240, 340, respectively. The terms "second inner cylindrical body," "inferior inner cylindrical body," and "third cylindrical body" may be used interchangeably as they have essentially the same meaning herein. The intermediate adjustment members 240, 340 are of the type described above with reference to the intermediate adjustment member 40 of implant 10 depicted in FIGS. 1-14. The first inner cylindrical body 250 may also be coupled to a first end member 20 with the first fastener 110 and the second inner cylindrical body 350 may also be coupled to a second end member 220 with the second fastener 210. The end members 210, 220 having the same limitations and functionality as those described above with reference to the implant 200 depicted in FIGS. 15-22.

Figure 25:
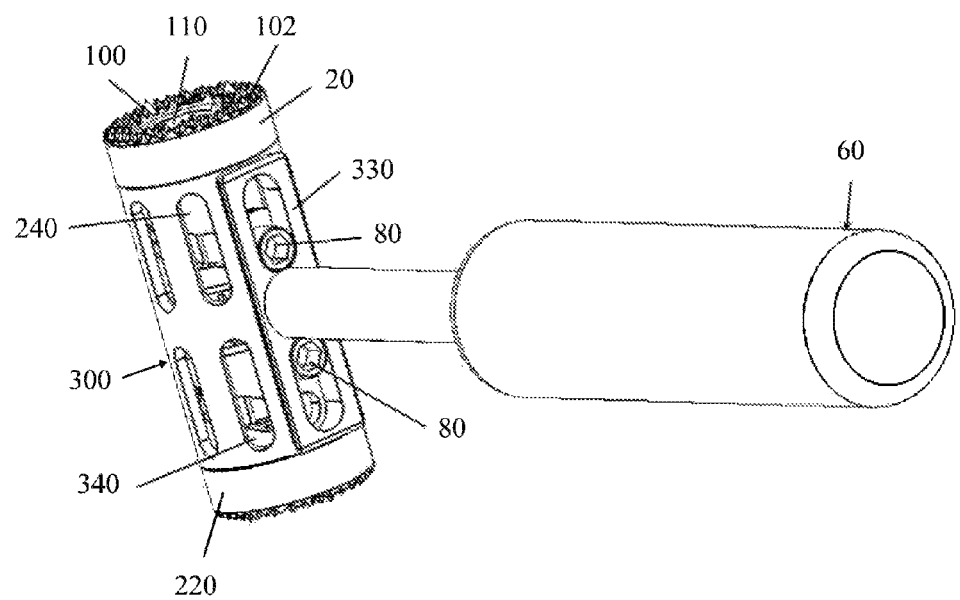
FIG. 25 is a perspective view of another embodiment of a tissue spacer device and a tool inserted into the tissue spacer device, in accordance with an aspect of the present invention.
Figure 26:
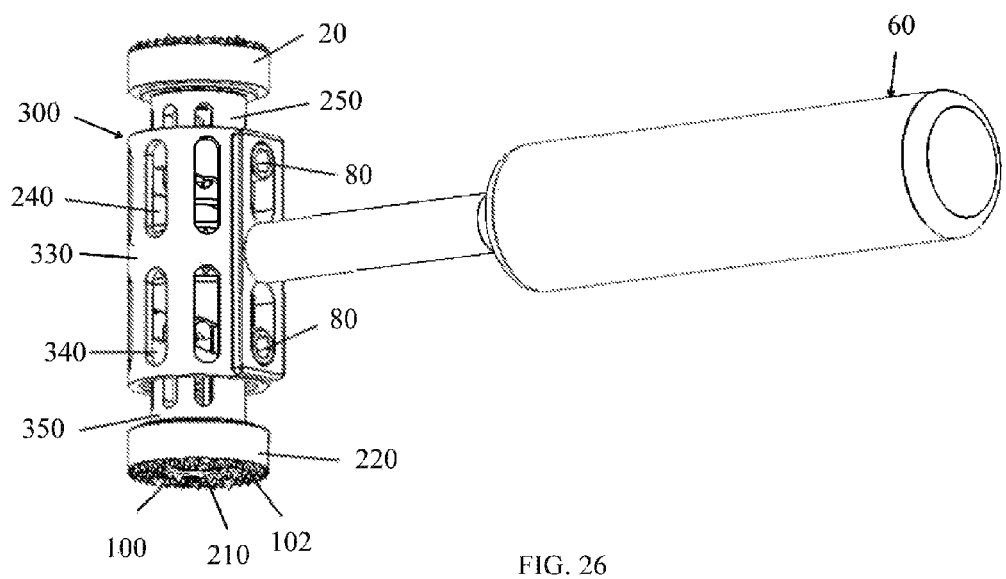
FIG. 26 is a perspective view of the tissue spacer device of FIG. 25 in a fully expanded position and the tool of FIG. 25, in accordance with an aspect of the present invention.
Figure 27:
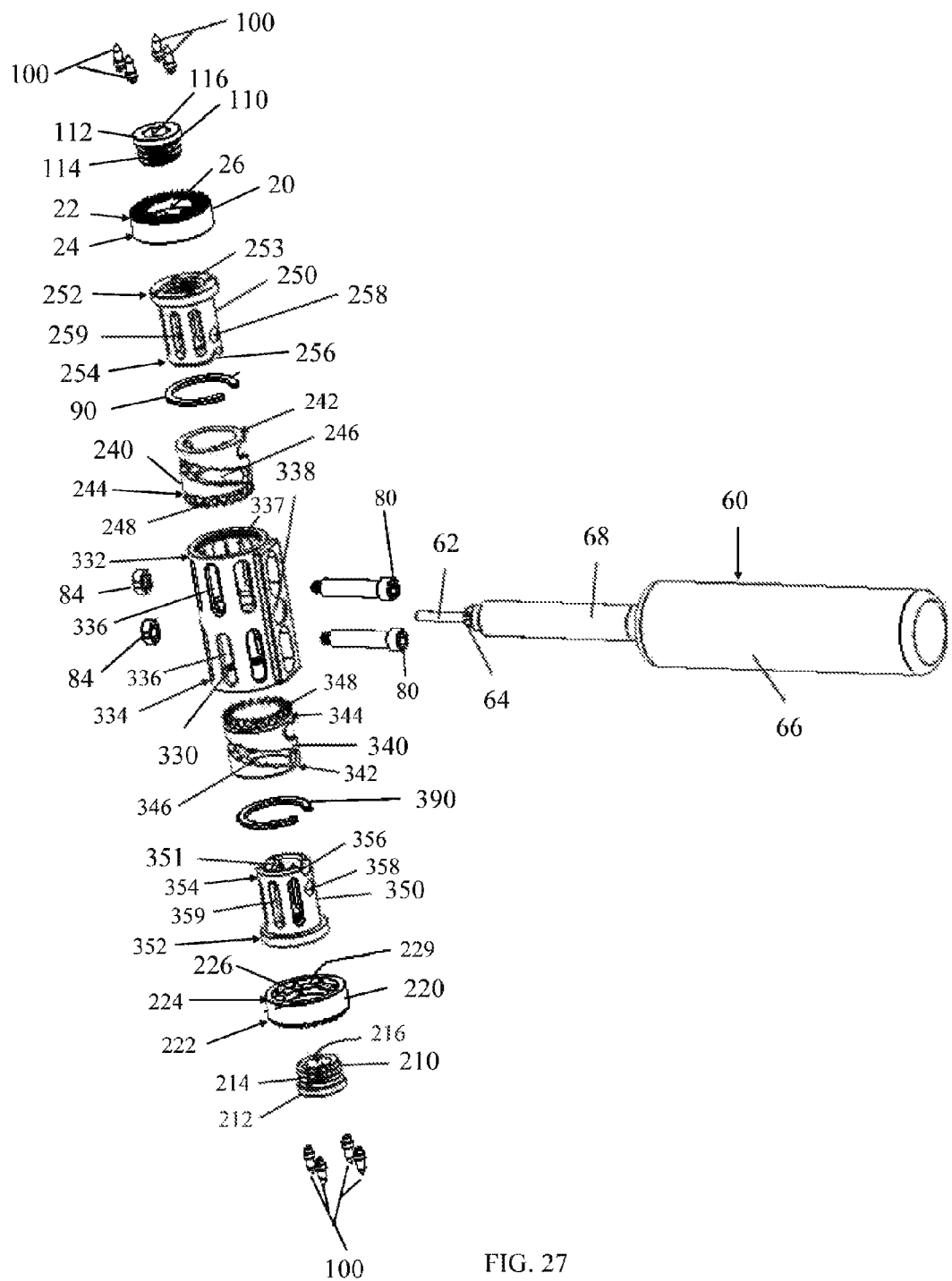
FIG. 27 is a fully exploded top perspective view of the tissue spacer device and tool of FIG. 25, in accordance with an aspect of the present invention.
Figure 28:
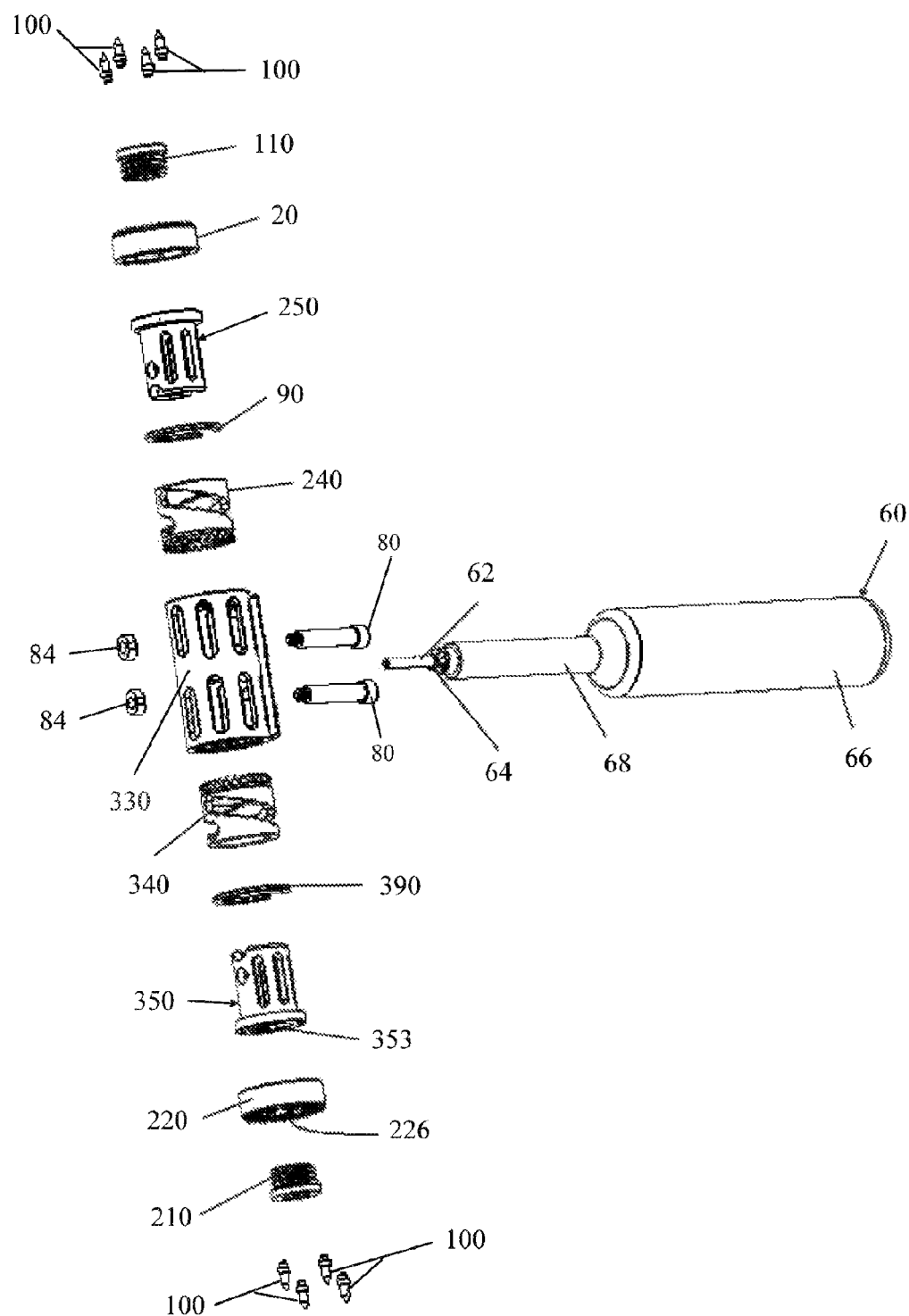
FIG. 28 is a fully exploded bottom perspective view of the tissue spacer device and tool of FIG. 25, in accordance with an aspect of the present invention.
Figure 29:
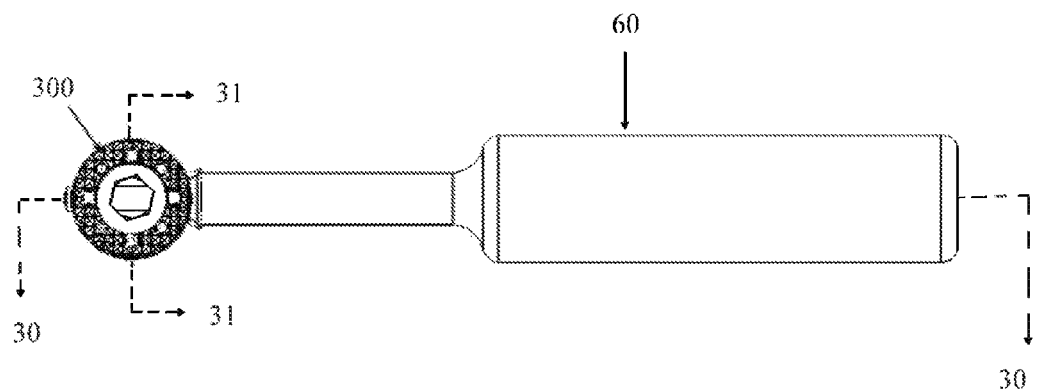
FIG. 29 is a top view of the tissue spacer device and tool of FIG. 25, in accordance with an aspect of the present invention.

As seen in FIGS. 25 and 26, respectively, the implant 300 is in the fully retracted position and fully extended position. In order to adjust the height of the implant 300 a tool, for example, the adjustment tool 60 or insertion tool 400, may be inserted into opening 338, shown in FIG. 27. The adjustment tool 60 including a guide pin 62, a plurality of gear teeth 64, a handle 66 and a connector rod 68, as described above with reference to FIGS. 3-7. The connector rod 68 is located intermediate and connects the guide pin 62 and the handle 66. The gear teeth 64 being located at the point where the connector rod 68 meets the guide pin 62. The insertion tool 400 will be discussed in greater detail below.

Figure 30:
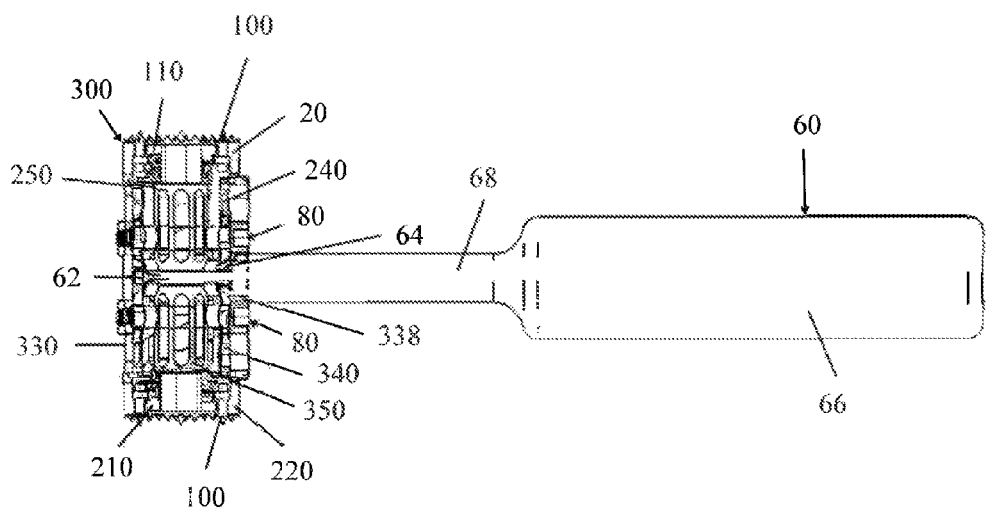
FIG. 30 is a cross sectional view of the device shown in FIG. 25 as viewed along section lines 30-30 in FIG. 29, in accordance with an aspect of the present invention.
Figure 31:
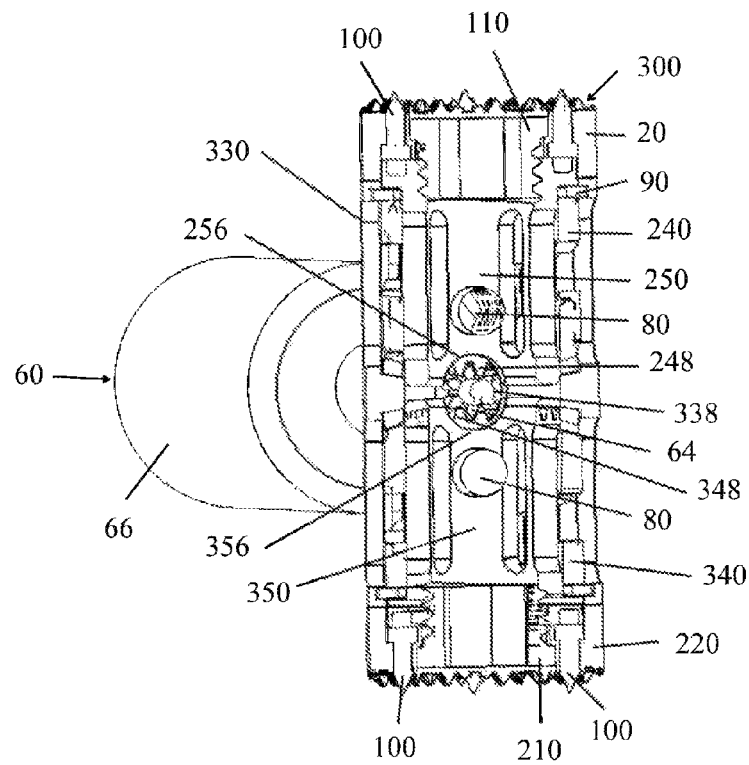
FIG. 31 is a cross sectional view of the device shown in FIG. 25 as viewed along section lines 31-31 in FIG. 29, in accordance with an aspect of the present invention.

As seen in the sectional views of FIGS. 30 and 31, when the guide pin 62 is inserted into opening 338 it passes between the adjustment members 240 and 340 and the cutouts 256 and 356 of the inner cylindrical bodies 250 and 350. Once the adjustment tool 60 is completely inserted into the opening 338, the gear teeth 64 of the adjustment tool 60 interface with the teeth-like or gear structures 248 and 348 of the adjustment members 240 and 340, respectively. As the handle 66 is rotated the gear teeth 64 mate with the teeth-like or gear structures 248 and 348 to rotate the adjustment members 240 and 340, respectively. The adjustment members 240 and 340 will turn in opposite directions as they rotate when the superior travel mechanism 80 is inserted into the lowest point of the diagonal slots 246 on the second end 244 of the adjustment member 240 and the inferior travel mechanism 80 is inserted into the highest point of the diagonal slots 346 on the second end 344 of the adjustment member 340. As the intermediate adjustment members 240, 340 turn they cause the superior and inferior fixed travel mechanisms 80 to slide along the paths of the diagonal openings 246, 346. As the travel mechanisms 80 move along the diagonal slots 246, 346 the inner cylindrical bodies 250, 350 moves either upward or downward depending on the direction of rotation, because the travel mechanisms 80 are coupled to the inner cylindrical bodies 250, 350. The end member 20 may move away or move towards the first end 332 of the outer body 330 and the opposing end member 220 may also move away or move towards the second end 334 of the outer body 330, either lengthening or shortening the implant 300, as shown in FIGS. 25 and 26.

Figure 37:
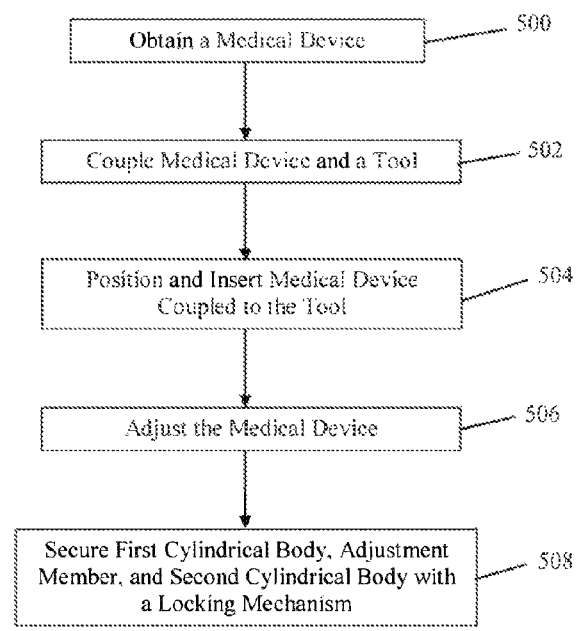
FIG. 37 depicts one embodiment of a surgical method for implanting a tissue spacer device into a patient's body, in accordance with an aspect of the present invention.

The appropriate surgical exposure and dissection techniques for the example surgical method using the tissue spacer implant 10, 200 or 300 are well known in the art. As shown in FIG. 37, the surgical method for using the implant 10, 200 or 300 may include the step 500 of obtaining a properly sized and configured implant 10, 200, or 300. The method may also include assembling the implant 10, 200, or 300 by selecting an end member 20 and attaching the selected end member 20 to the inner cylindrical body 50, 250. The assembling step may further include selecting a fastener 110 and inserting the fastener 110 through the opening 26 in the end member 20 and into the central cavity 51, 251 of the inner cylindrical body 50, 250 to engage the threads 53, 253. If implant 200 is being used, the assembly step may also include selecting a second end member 220 and attaching the selected second end member 220 to the second end 234 of the elongated cylindrical body 230. The assembling step for implant 200 may also include selecting a second fastener 210 and inserting the second fastener 210 through the opening 226 in the second end member 220 and into the central cavity 231 to engage the inner threads 235 of the elongated cylindrical body 230. If the implant 300 is being used, the assembly step may also include selecting a second end member 220 and attaching the selected second end member 220 to the second inner cylindrical body 250. The assembling step for implant 300 may further include selecting a second fastener 210 and inserting the second fastener 210 through the opening 226 in the end member 220 and into the central cavity 351 of the inner cylindrical body 350 to engage the threads 353.

Once the tissue spacer implant 10, 200, or 300 is assembled, the next step 502 may include attaching the tissue spacer implant 10, 200, or 300 to an insertion tool, for example, insertion tool 400 described in greater detail below. Following the attachment of the tissue spacer implant 10, 200, or 300 to the insertion tool 400, the next step 504 includes placing the implant 10, 200 or 300 between two tissue bodies. For example purposes only, we shall describe herein the technique as used in the replacement of a missing vertebral body. The end of the insertion tool 400 with the coupled and aligned implant 10, 200 or 300 is positioned within a space within a spinal column. If implant 10 is used the end member 20 and outer cylindrical body 30 may be positioned to engage respective adjacent vertebral bodies. Alternatively, if implant 200 or 300 is used the end member 20 and the second end member 220 may be positioned to engage respective adjacent vertebral bodies. An adjustment tool 60 may then be used during step 506 to complete the distraction step or maintenance of the existing space by lengthening or shortening the implant 10, 200, or 300, as described above, to the desired height to enable the end member 20 and the outer cylindrical body 30 or first and second end members 20, 220 to sufficiently engage the respective adjacent vertebral bodies. The positioning mechanism 440 of the insertion tool 400 may alternatively be used in place of the adjustment tool 60 in the currently described methods, as described in greater detail below. Once the desired length is achieved, step 508 may include securing a travel mechanism 80 before or after a tool, for example, the adjustment tool 60, is removed to prevent rotational movement of the intermediate adjustment member 40, 240, 340. If the adjustment tool 60 is removed prior to fixing the travel mechanism 80, once the travel mechanism 80 is secured, the implant 10, 200, 300 is fixed at the required length to maintain the necessary space between the two vertebral bodies. The travel mechanism 80 may be tightened to fix the implant 10, 200, or 300 at a desired height. If the adjustment tool 60 is removed after securing the travel mechanism 80, the method may further include the step of fixing the travel mechanism 80 onto the outer cylindrical body 30, 230, 330 and securing the intermediate adjustment member 40, 240, 340 in position between the outer cylindrical body 30, 230, 330 and the inner cylindrical body 50, 250, 350, to secure the implant 10, 200, 300 at a desired height between two vertebral bodies within a patient's spinal column. The method may further include the step of removing the adjustment tool 60 or insertion tool 400 from the outer cylindrical body 30, 230, 330 of the implant 10, 200, 300 and removing the adjustment tool 60 from inside the living body.

It should be understood by those skilled in the art that the surgical method described herein may also include using alternative embodiments of end members 20, 220 to accommodate various clinical deformities or bone growth coatings.

Referring now to FIGS. 32-36, an alternative insertion tool 400 and locking instrument 470 are shown. The insertion tool 400 and locking instrument 470 engaging the implant 10 is shown in FIG. 32. The insertion tool 400 includes a handle 402 coupled to a housing 430 which may receive a positioning mechanism 440 and an insertion mechanism 450. The handle 402 may include a proximal handle portion 404 and a distal handle portion 406. The distal handle portion 406 may have a first opening 408 along the longitudinal axis of the handle 402 for receiving the proximal handle portion 404. The proximal handle portion 404 may be secured to the distal handle portion 406 using fasteners, for example, screws (not shown). The distal handle portion 406 may also include a second opening 410 along the longitudinal axis of the handle 402 and opposite the first opening 408 for receiving the housing 430 and the insertion mechanism 450. The proximal handle portion 404 may have a through hole 412 along the longitudinal axis of the handle 402 for receiving the positioning mechanism 440 and engaging the insertion mechanism 450 at a distal end of the through hole 412 of the proximal handle portion 404.

The proximal handle portion 404 may also include an opening 414 perpendicular to and engaging the through hole 412. The opening 414 is configured to receive the actuation button 420.

Figure 34:
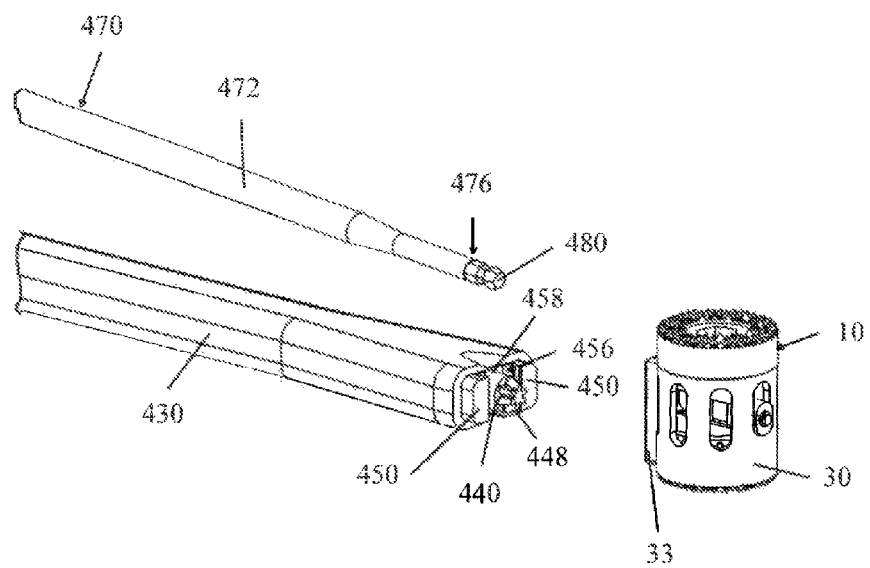
FIG. 34 is a truncated perspective view of the insertion tool and locking instrument of FIG. 32 and the tissue spacer device of FIG. 1, in accordance with an aspect of the present invention.
Figure 35:
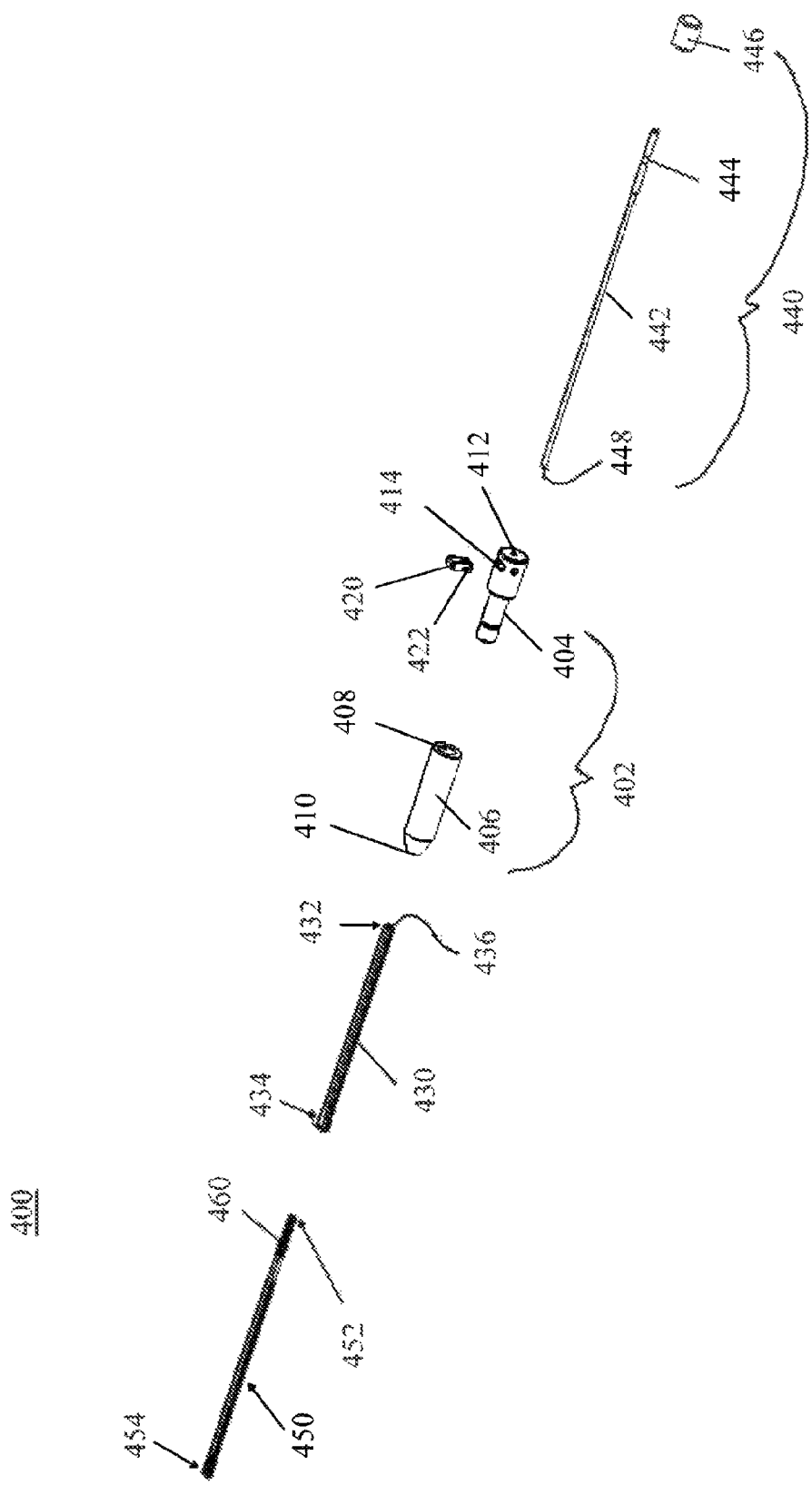
FIG. 35 is an exploded perspective view of the insertion tool of FIG. 32, in accordance with an aspect of the present invention.
Figure 36:
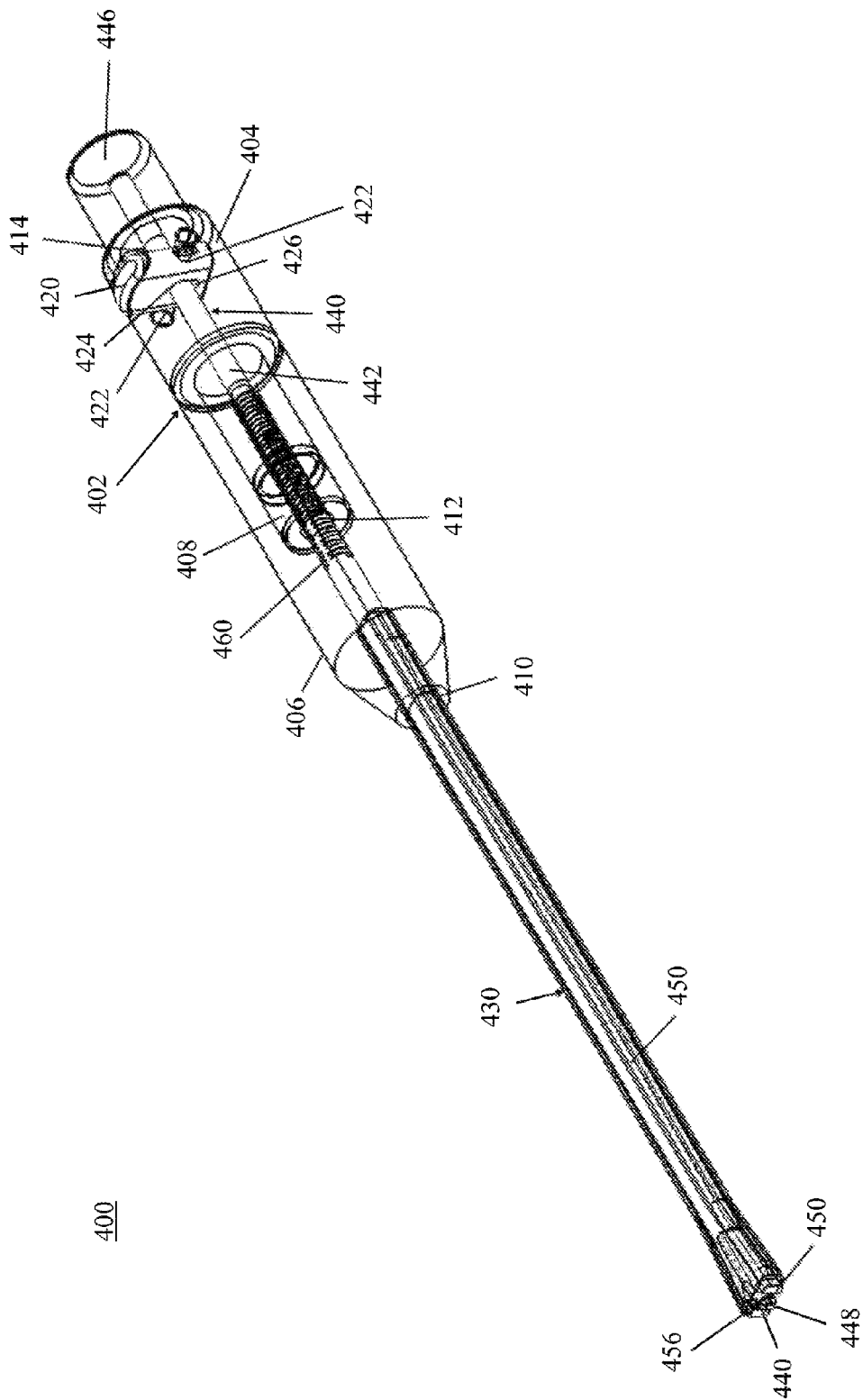
FIG. 36 is a perspective view of the insertion tool of FIG. 32 with a transparent handle, outer housing and knob, in accordance with an aspect of the present invention.

Referring now to FIG. 36, the actuation button 420 may include two side channels 422 that engage fasteners for securing the actuation button 420 to the handle 402 and the two side channels 422 are configured to enable the fasteners to slide along the channels 422 allowing the actuation button 420 to move. The actuation button 420 may also include an opening 424 with a locking channel 426 for securing the positioning mechanism 440 in the handle 402 of the insertion tool 400. As seen in FIGS. 34-36, the positioning mechanism 440 may include a shaft 442 with a channel 444 at the proximal end of the shaft 442 for engaging the opening 424 and locking channel 426 of the actuation button 420. The positioning mechanism 440 may also include a knob 446 which couples to the proximal end of the shaft 442. The shaft 442 of the positioning mechanism 440 may also include a plurality of gear teeth 448 at the distal end of the shaft 442. The plurality of gear teeth 448 of the shaft 442 of the positioning mechanism 440 are configured to engage the teeth-like or gear structures 48 of the intermediate adjustment mechanism 40 of the implant 10.

The positioning mechanism 440 may pass through the handle 402 and then through the insertion mechanism 450 to enable engagement with the adjustment mechanism 40 of the implant 10. The insertion mechanism 450 may include a proximal end 452 and a distal end 454 as shown in FIG. 35. The distal end 454 may include a threaded end 460 for engaging corresponding threads within the distal end of the through hole 412 of the proximal handle portion 406. As shown in FIG. 34, the insertion mechanism 450 may also include a through opening 458 running along the longitudinal axis of the insertion mechanism 450. The shaft 442 of the positioning mechanism 440 may pass through the through opening 458 of the insertion mechanism 450. The insertion mechanism 450 may further include an engagement channel 456 on the proximal end 452 of the insertion mechanism 450 for mating with the engagement boss 33 on the exterior surface of the outer cylindrical body 30 of the implant 10, as shown in FIG. 32.

The insertion mechanism 450 may fit within the housing 430 of the insertion tool 400 as shown in FIG. 36. The housing 430 may include a proximal end 432 that couples to the distal handle portion 406 and a distal end 434, as shown in FIG. 35. The housing 430 may be secured to the distal handle portion 406 using fasteners, for example, screws (not shown). The housing 430 may also include a through hole 436 passing from the proximal end 432 to the distal end 434 along the longitudinal axis of the housing 430. The insertion mechanism 450 may be inserted into the through hole 436 from the distal end 434 of the housing 430 and pass out of the housing 430 at the proximal end 432 to engage the proximal handle portion 404. Once the housing 430 and insertion mechanism 450 are coupled to the handle 402, the engagement channel 456 of the insertion mechanism 450 of the insertion tool 400 may be attached to the engagement boss 33 on the outer cylindrical body 30 of the implant 10.

Figure 33:
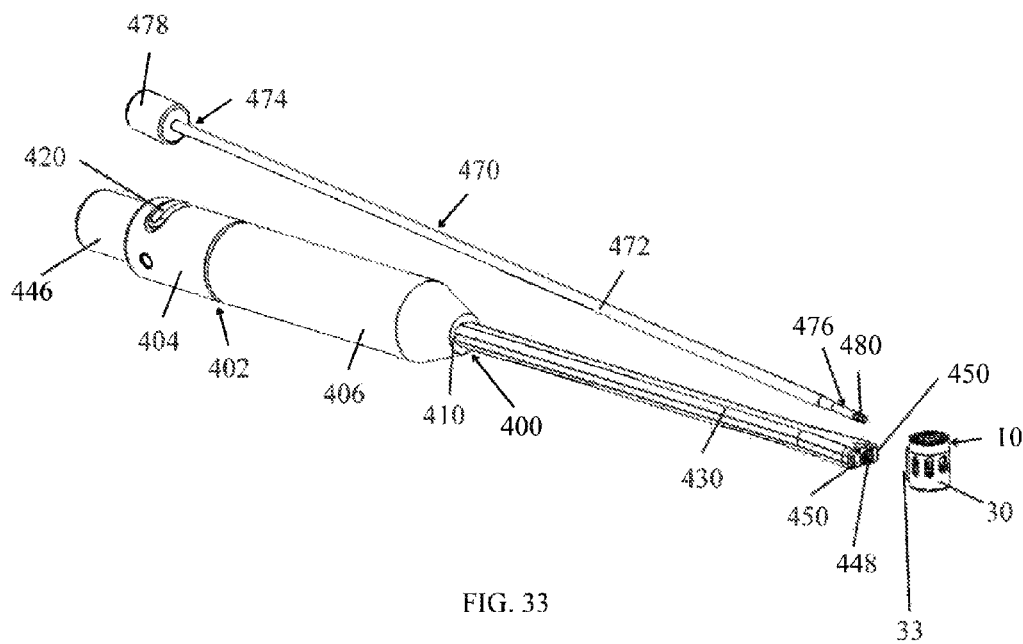
FIG. 33 is a partially exploded, perspective view of the insertion tool and locking instrument of FIG. 32 and the tissue spacer device of FIG. 1, in accordance with an aspect of the present invention.

The locking instrument 470 may include a shaft 472 with a proximal end 474 and a distal end 476, as seen in FIGS. 32-34. The locking instrument 470 may include a knob 478 at the proximal end 474 of the shaft 472 for adjusting the travel mechanism 80 of the implant 10. The locking instrument 470 may also include an engagement end 480 at the distal end 476 of the shaft 472. The engagement end 480 may be configured to engage the head portion 82 of the travel mechanism 80. The engagement end 480 may include a head that enables rotation of the head portion 82 of the travel mechanism 80 at an angle, as shown in FIG. 32, to enable the use of the insertion tool 400 and the locking instrument 470 simultaneously. The engagement end 480 may, for example, have a hexagon, square, or other multi-lobed configuration allowing the engagement end 480 to engage the head portion 82 to tighten the travel mechanism 80 and engagement member 84 to secure the implant 10 in the desire extension or retraction.

The insertion tool 400 and locking instrument 470 may also be used in the above described surgical method in place of the adjustment tool 60. Prior to inserting the positioning mechanism 440, the insertion tool 400 may be secured to the implant 10 by sliding the engagement boss 33 of the implant 10 into engagement with the engagement channel 456 of the insertion mechanism 450. Next, the positioning mechanism 440 may be inserted into the handle 402 of the insertion tool 400 and slid through the insertion mechanism 450 inside the housing 430 of the insertion tool 400 to engage the plurality of gear teeth 448 of the shaft 442 of the positioning mechanism 440 with the teeth-like or gear structures 48 of the intermediate adjustment mechanism 40 of the implant 10. Once the implant 10 is secured to the insertion tool 400, the implant 10 may be inserted into the patient between two vertebrae. After inserting the implant 10, the physician may adjust the height of the implant 10 by rotating the knob 446 of the positioning mechanism 440 thereby rotating the gear teeth 448 which are engaging the teeth-like or gear structures 48 of the adjustment mechanism 40 to rotate the intermediate adjustment mechanism 40. As the adjustment mechanism 40 turns, the fixed travel mechanism 80 slides along the path of the diagonal openings 46 causing the coupled inner cylindrical body 50 to move in an upward or downward direction depending on the direction of rotation of the gear teeth 448. When a desired length of the implant 10 is achieved, the engagement end 480 of the locking instrument 470 may be inserted to engage the corresponding opening in the fastener 82 of the travel mechanism 80 to tighten the travel mechanism 80 thereby securing the intermediate adjustment member 40 to the outer cylindrical body 30 and inner cylindrical body 50 to prevent additional rotation of the adjustment member 40. After the implant 10 has been secured in the desired position, the locking instrument 470 may be removed from the patient and the positioning mechanism 440 may be removed from the insertion tool 400. Next the insertion tool 400 may be slid to disengage the engagement channel 456 of the insertion mechanism 450 from the engagement boss 33 of the implant 10 and the insertion tool 400 may be removed from the patient. The patient's incision may then be closed.

Figure 40:
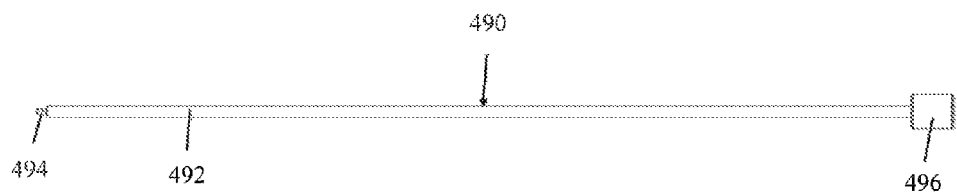
FIG. 40 is a side view of a locking mechanism inserter, in accordance with an aspect of the present invention.
Figure 42:
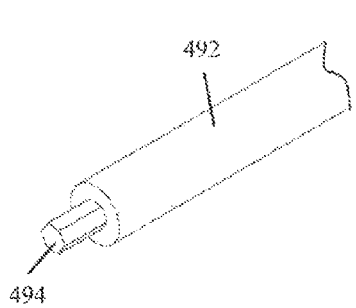
FIG. 42 a truncated perspective view of the engagement end of the locking mechanism inserter of FIG. 38, in accordance with an aspect of the present invention.
Figure 44:
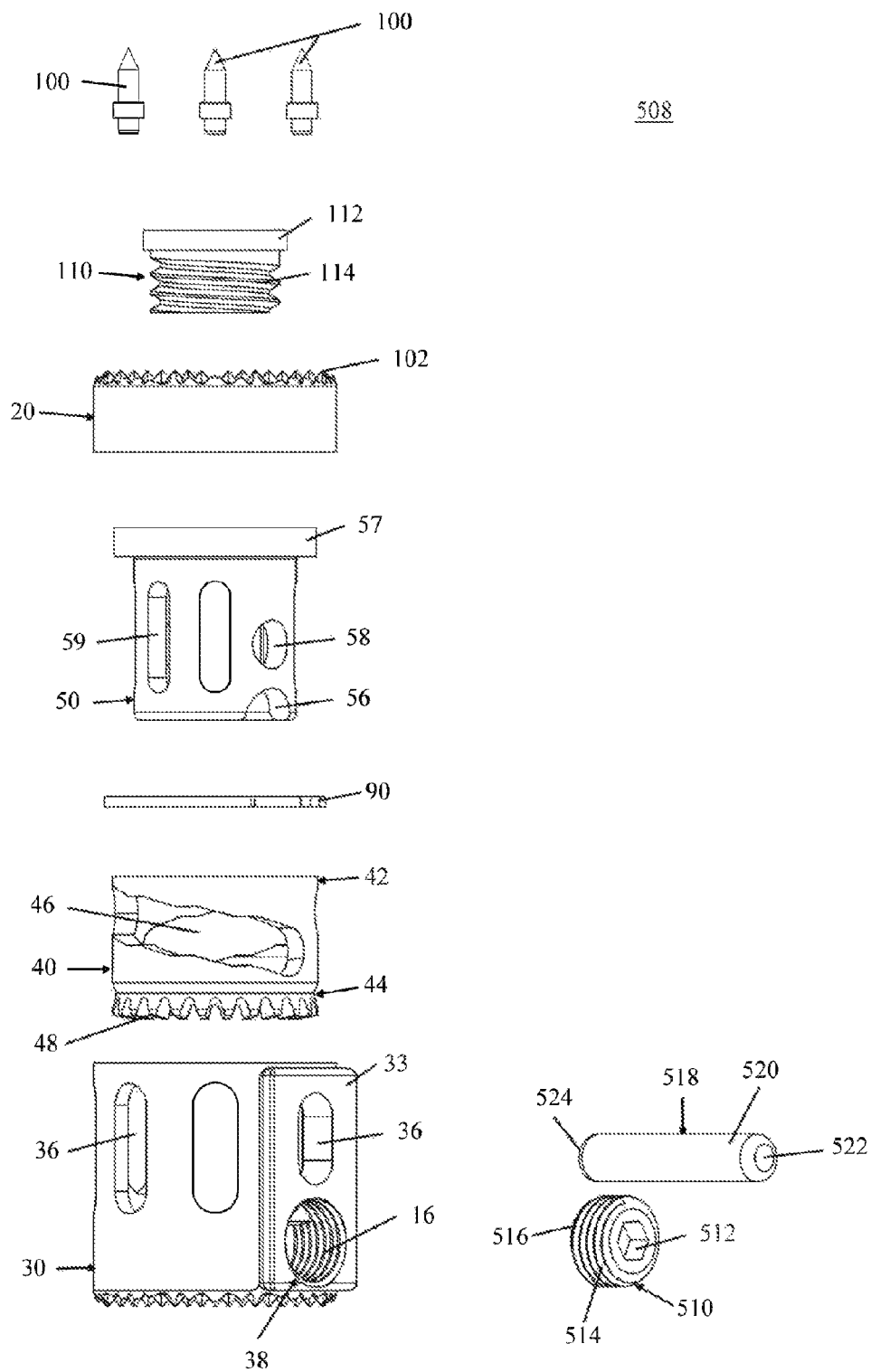
FIG. 44 is a fully exploded side, perspective view of an alternative tissue spacer device, in accordance with an aspect of the present invention.

Referring now to FIGS. 40 and 42, a first locking mechanism inserter 490 is shown. The locking mechanism inserter 490 may include a shaft 492 with an engagement end 494 at a first end and a knob 496 at a second end. As shown in FIG. 42, the engagement end 494 may have a shape corresponding to the shape of an opening 512 in a first locking mechanism 510, shown in FIG. 44. The first locking mechanism 510 may be used with an alternative embodiment tissue spacer implant 508. The implant 508 is similar to the implant 10 described above, however the implant 508 includes an alternative travel mechanism 518. As shown in FIG. 39, the alternative travel mechanism 518 includes a shaft 520 with a first end 522 and a second end 524. The second end 524 of the travel mechanism 518 may be inserted through the shorter vertical opening 36 in the outer cylindrical body 30, one of the two helical openings 46, through two parallel elongated vertically oriented openings 59, through a second of the two helical openings 46, and into a second vertical opening 36 parallel to the shorter vertical opening 36. In addition, the adjustment opening 38 in the implant 508 may include threads 16 for engaging the first locking mechanism 510. The first locking mechanism 510 includes a drive opening 512, exterior threads 514, and an impact end 516. As discussed above, the drive opening 512 is shaped to correspond to the shape of the engagement end 494 of the inserter 490. The exterior threads 514 may engage the interior threads 16 of the adjustment opening 38. The impact end 516 is configured to engage the exterior surface of the second end 44 of the intermediate adjustment member 40 to prevent the adjustment member 40 from rotating.

Once the implant 508 is assembled, the implant 508 may be inserted into a patient using the insertion tool 400. The positioning mechanism 440 (see FIGS. 34-36) may be used to increase or decrease the height of the implant 508, as described above. After the implant 508 is adjusted to a desired height, the positioning mechanism 440 may be removed from the insertion tool 400. The physician may then attach the engagement end 494 of the first locking mechanism inserter 490 to the drive opening 512 of the first locking mechanism 510. Once the first locking mechanism 510 is coupled to the first inserter 490, the first inserter 490 may be inserted into the tool 400. The first inserter 490 is inserted into the hole 412 in handle 402 and through the insertion mechanism 450 to enable insertion of the first locking mechanism 510 into the adjustment opening 38 to engage the intermediate adjustment member 40. The threads 514 of the first locking mechanism 510 will engage the interior threads 16 of the opening 38 by rotating the knob 496 of the first inserter 490. Once the first locking mechanism 510 is inserted into the opening 38, the impact end 516 contacts the intermediate adjustment member 40 to secure the adjustment member 40 in the selected position to maintain the desired height of the implant 508. The first inserter 490 may then be removed from the insertion tool 400, the insertion tool 400 may be detached from the implant 508, and the patient closed.

Figure 41:
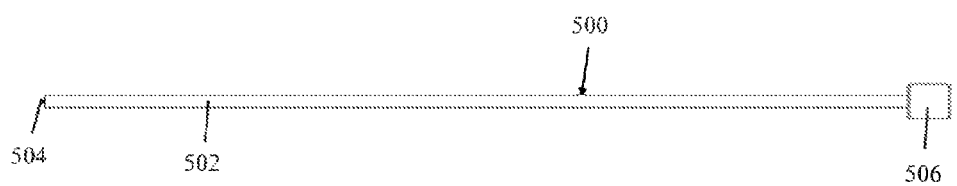
FIG. 41 is a side view of an alternative locking mechanism inserter, in accordance with an aspect of the present invention.
Figure 43:
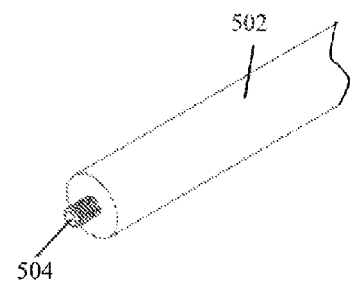
FIG. 43 a truncated perspective view of the engagement end of the locking mechanism inserter of FIG. 39, in accordance with an aspect of the present invention.
Figure 45:
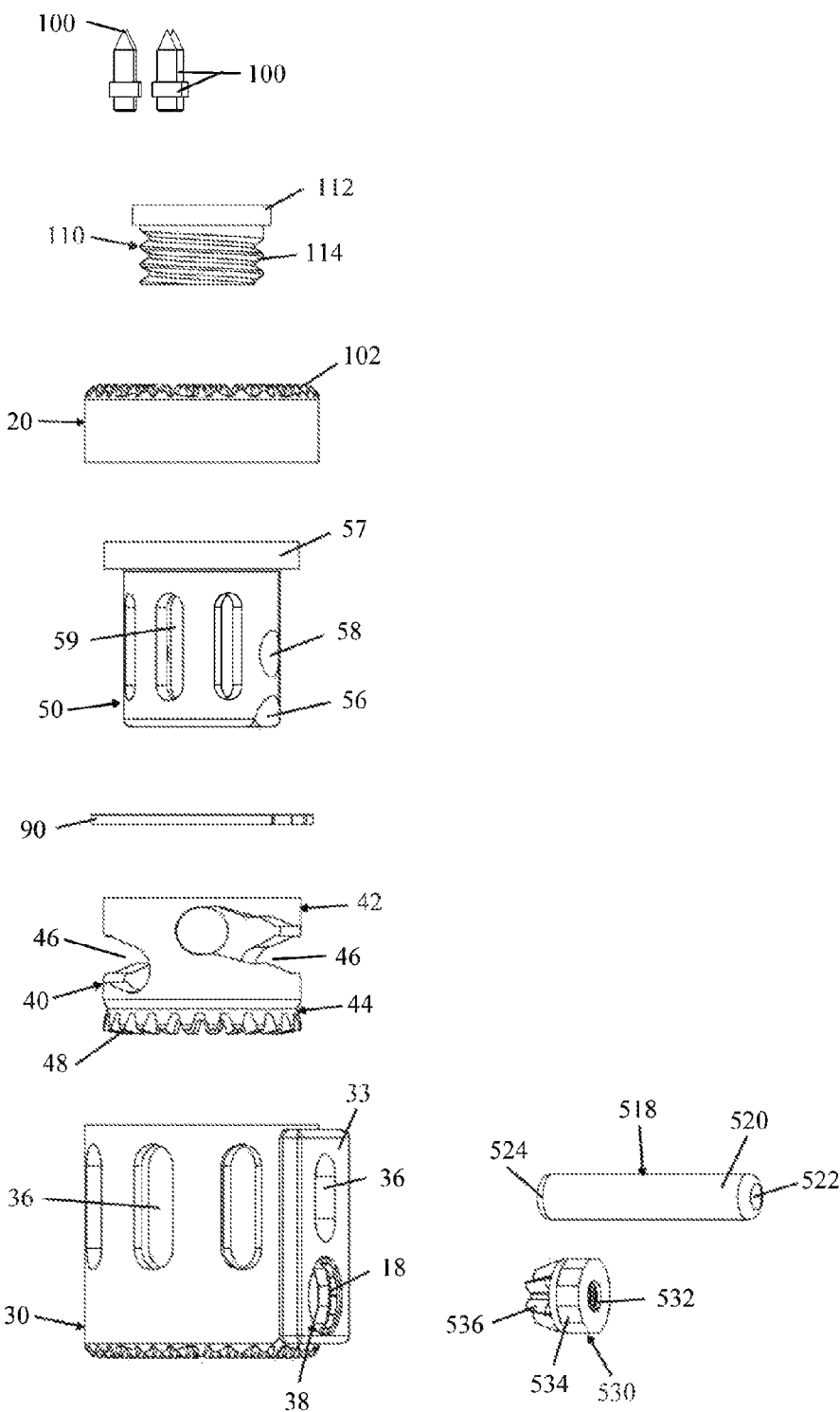
FIG. 45 is a fully exploded side, perspective view of another alternative tissue spacer device, in accordance with an aspect of the present invention.

A second locking mechanism inserter 500 is shown in FIGS. 41 and 43. The second locking mechanism inserter 500 may include a shaft 502 with an engagement end 504 at a first end and a knob 506 at a second end. As shown in FIG. 43, the engagement end 504 may be threaded to engage an opening 532 in a second locking mechanism 530, shown in FIG. 45. The second locking mechanism 530 may be used with another alternative embodiment tissue spacer implant 528. The implant 528 is similar to the implant 508 with the alternative travel mechanism 518 described above, however the implant 528 includes an alternative adjustment opening 38 including a lip 18. The lip 18 in the adjustment opening 38 is configured to engage the second locking mechanism 530. The second locking mechanism 530 includes an attachment opening 532 that may be threaded, an exterior surface 534, and a plurality of gear teeth 536. The gear teeth 536 are configured to engage the teeth-like or gear structures 48 of the intermediate adjustment member 40 to secure the adjustment member 40 to prevent additional rotation. The exterior surface 534 may be shaped to correspond to the shape of the adjustment opening 38 above the lip 18.

Once the implant 528 is assembled, the implant 528 may be inserted into a patient with the insertion tool 400. As discussed above, the positioning mechanism 440 (see FIGS. 34-36) may be used to increase or decrease the height of the implant 528. After the implant 528 is adjusted to a desired height, the positioning mechanism 440 may be removed from the insertion tool 400. The physician may then attach the second locking mechanism 530 to the second locking mechanism inserter 500 by rotating the threads of the engagement end 504 of the second locking mechanism 530 to engage the threads of the attachment opening 532 of the second inserter 500. Once the second locking mechanism 530 is secured to the second locking mechanism inserter 500, the second inserter 500 may be inserted into the insertion tool 400 to enable insertion of the second locking mechanism 530 into the adjustment opening 38 to engage the intermediate adjustment member 40. As the second locking mechanism 530 is inserted into the opening 38, the gear teeth 536 of the locking mechanism 530 will engage the teeth-like or gear structures 48 of the intermediate adjustment member 40 and the exterior surface 534 of the locking mechanism 530 will engage the lip 18 of the adjustment opening 38 of the implant 528. The gear teeth 536 and exterior surface 534 of the second locking mechanism 530 will engage the intermediate adjustment member 40 and the adjustment opening 38 of the implant 528 to lock the intermediate adjustment member 40 in the selected position to maintain a desired height of the implant 528. The second inserter 500 may then be removed from the locking mechanism 530 by rotating the knob 506 to remove the threads of the engagement end 504 from the threads of the attachment opening 532 of the second locking mechanism 530. Once the engagement end 504 of the second inserter 500 is removed from the second locking mechanism 530, the second inserter 500 may be removed from the insertion tool 400. After removing the second inserter 500, the insertion tool 400 may be detached from the implant 528 and the patient's incision closed.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

Although the example embodiments have been depicted and described in detail herein, it will be apparent to those skilled in the relevant art that various modifications, additions and substitutions can be made without departing from its essence and therefore these are to be considered to be within the scope of the following claims.

What is claimed is:

1. A tissue spacer implant, the implant comprising:
a first cylindrical body including an outer surface, an axially extending hole, and a first end;
a second cylindrical body including an outer surface and an axially extending hole;
an adjustment member including an outer surface, an axial hole extending from a first end to a second end, at least one diagonal slot extending partially around and entirely through the outer surface of the adjustment member, a circular cross-section, and gear structures on at least one of the first end and the second end, wherein the axial hole of the adjustment member is adapted to receive the first cylindrical body and the adjustment member is configured to be inserted into the axially extending hole of the second cylindrical body; and
a first travel mechanism engaging the first cylindrical body, the adjustment member, and the second cylindrical body along the at least one diagonal slot of the adjustment member to maintain a space between two bodies of tissue.

2. The tissue spacer implant of claim 1, wherein the first travel mechanism comprises a shaft with a first end and a second end.

3. The tissue spacer implant of claim 2, wherein the shaft of the first travel mechanism includes a head portion at the first end and a threaded portion at the second end, the threaded portion couples to an engagement member.

4. The tissue spacer implant of claim 2, wherein the first cylindrical body includes a plurality of openings and the second cylindrical body includes a plurality of vertical openings.

5. The tissue spacer implant of claim 4, wherein the shaft of the first travel mechanism extends through two vertical openings of the plurality of vertical openings in the second cylindrical body, the at least one diagonal slot of the adjustment member, and two openings of the plurality of openings in the first cylindrical body to couple the first cylindrical body, the second cylindrical body, and the adjustment member.

6. The tissue spacer implant of claim 1, further comprising:
a locking mechanism, wherein the second cylindrical body includes an adjustment opening, the adjustment opening is adapted to receive the locking mechanism to secure the adjustment member.

7. The tissue spacer implant of claim 6, wherein the locking mechanism includes a first end and a second end, the second end includes a plurality of gear teeth;
wherein the adjustment member further comprises gear structures extending from at least one of the first end and the second end; and
the plurality of gear teeth engage the gear structures.

8. The tissue spacer implant of claim 1, further comprising:
a channel in the axial hole of the second cylindrical body; and
a support means adapted to engage the channel and provide a bearing surface for the adjustment member.

9. The tissue spacer implant of claim 1, further comprising:
a first end member configured to engage the first end of the first cylindrical body, wherein the first end member includes an axially extending hole with an interior lip.

10. The tissue spacer implant of claim 9, further comprising:
a fastener including a collar and a threaded portion, wherein the fastener couples the first end member to the first cylindrical body; and
wherein the first end member is coupled to the first cylindrical body by inserting the fastener into the axially extending hole of the first end member and the axially extending hole of the first cylindrical body, the collar of the fastener being adapted to engage the interior lip in the axially extending hole of the first end member and the threaded portion of the fastener configured to engage corresponding threads in the axially extending hole of the first cylindrical body.

11. The tissue spacer implant of claim 1, wherein the second cylindrical body includes an engagement end having a rim and a threaded portion, the threaded portion disposed within the axially extending hole.

12. The tissue spacer implant of claim 11, further comprising:
a second end member including an axially extending hole with an interior lip and configured to engage the engagement end of the second cylindrical body; and
a second fastener including a collar and a threaded portion, wherein the second fastener is adapted to couple the second end member to the second cylindrical body.

13. The tissue spacer implant of claim 1, further comprising:
a third cylindrical body including an outer surface, an axially extending hole, and a first end;
a second adjustment member including an outer surface, an axially extending hole, and at least one diagonal slot extending partially around the outer surface of the second adjustment member, the axially extending hole of the second adjustment member is adapted to receive the third cylindrical body and the second adjustment member is configured to be inserted into the axially extending hole of the second cylindrical body opposite the coupled first cylindrical body and the adjustment member; and
a second travel mechanism for securing the third cylindrical body, the second adjustment member, and the second cylindrical body at a desired position along the at least one diagonal slot of the second adjustment member to maintain a space between two bodies of tissue.

14. The tissue spacer implant of claim 13, wherein the second travel mechanism comprises a shaft with a first end and a second end.

15. The tissue spacer implant of claim 14, wherein the shaft of the second travel mechanism extends through two vertical openings of the plurality of vertical openings in the second cylindrical body, the at least one diagonal slot of the second adjustment member, and two openings of a plurality of openings in the third cylindrical body to couple the second cylindrical body, the third cylindrical body, and the adjustment member.

16. The tissue spacer implant of claim 13, further comprising:
a second end member configured to engage the first end of the third cylindrical body; and
a second fastener including a collar and a threaded portion, the second fastener being configured to couple the second end member to the third cylindrical body.

17. A tissue spacer implant, the implant comprising:
at least one inner cylindrical body having an outer surface, an axially extending hole, and a first end;
an outer cylindrical body having an outer surface and an axially extending hole;
at least one adjustment member having an outer surface, an axially extending hole, and at least one helical slot extending partially around and entirely through the outer surface of the at least one adjustment member, a circular cross-section, and gear structures on at least one of a first end and a second end, wherein the axially extending hole of the at least one adjustment member is configured to receive the at least one inner cylindrical body and the at least one adjustment member is sized to be inserted into the axially extending hole of the outer cylindrical body; and
at least one travel mechanism comprised of a shaft, the shaft passing through the at least one inner cylindrical body, the at least one adjustment member, and the outer cylindrical body to maintain a desired position along the at least one helical slot of the at least one adjustment member.

18. The tissue spacer implant of claim 17, wherein the at least one inner cylindrical body includes at least two openings, the outer cylindrical body includes at least two oblong openings, and the shaft of the at least one travel mechanism extends through the two oblong openings in the outer cylindrical body, the at least one helical slot of the at least one adjustment member, two openings in the at least one inner cylindrical body to couple the outer cylindrical body, the at least one inner cylindrical body, and the at least one adjustment member.

19. A surgical method for maintaining a space between two tissue bodies in a living being, comprising:
obtaining a medical device, comprising:
a first cylindrical body including an outer surface, an axially extending hole, and a first end;
a second cylindrical body including an outer surface and an axially extending hole;
an adjustment member including an outer surface, an axial hole extending from a first end to a second end, at least one helical slot extending partially around and entirely through the outer surface of the adjustment member, a circular cross-section, and gear structures on at least one of the first end and the second end, wherein the axial hole of the adjustment member is adapted to receive the first cylindrical body and the adjustment member is configured to be inserted into the axially extending hole of the second cylindrical body; and
a first travel mechanism engaging the first cylindrical body, the adjustment member, and the second cylindrical body along the at least one helical slot of the adjustment member to maintain a space between two bodies of tissue;
coupling the second cylindrical body to a tool;
positioning and inserting the tool with the medical device in a retracted position into a space between the two tissue bodies to maintain or increase the space therebetween;
adjusting the medical device along the at least one helical slot of the adjustment member to a desired length; and
securing the first cylindrical body, the adjustment member and the second cylindrical body using a locking mechanism at the desired length.

* * * * *